United States Patent [19]

Monard et al.

[11] Patent Number: 5,656,596
[45] Date of Patent: *Aug. 12, 1997

[54] METHOD OF TREATING LESIONS IN A NERVOUS SYSTEM

[75] Inventors: Denis Monard, Füllinsdorf; Karel Gerrit Odink, Rheinfelden; Sergio Gloor, Basel, all of Switzerland

[73] Assignee: Incyte Pharmaceuticals, Inc., Palo Alto, Calif.

[*] Notice: The term of this patent shall not extend beyond the expiration date of Pat. No. 5,112,608.

[21] Appl. No.: 439,704

[22] Filed: May 12, 1995

Related U.S. Application Data

[63] Continuation of Ser. No. 192,808, Feb. 8, 1994, abandoned, which is a continuation of Ser. No. 8,819, Jan. 30, 1987, abandoned.

[30] Foreign Application Priority Data

| Feb. 4, 1986 | [GB] | United Kingdom | 8602626 |
| Feb. 11, 1986 | [GB] | United Kingdom | 8603354 |
| Jul. 31, 1986 | [GB] | United Kingdom | 8618760 |

[51] Int. Cl.$^6$ ............................................. A61K 38/18
[52] U.S. Cl. ........................... 514/12; 514/2; 530/399; 435/69.4; 536/23.51; 536/23.5; 930/120
[58] Field of Search ................... 514/2, 12; 530/399; 536/23.51, 23.5; 435/69.4; 930/120

[56] References Cited

U.S. PATENT DOCUMENTS

| 3,985,722 | 10/1976 | Yoshida et al. | 530/360 |
| 4,394,443 | 7/1983 | Weissman et al. | 435/6 |
| 4,468,464 | 8/1984 | Cohen et al. | 435/320.1 |
| 4,556,643 | 12/1985 | Paau et al. | 436/5 |
| 4,703,107 | 10/1987 | Monsigny et al. | 530/330 |
| 5,112,608 | 5/1992 | Scott et al. | 424/94.64 |
| 5,278,049 | 1/1994 | Baher et al. | 435/68.1 |

FOREIGN PATENT DOCUMENTS

| 0 251 505 | 6/1987 | European Pat. Off. |
| 0251505 | 1/1988 | European Pat. Off. |

OTHER PUBLICATIONS

D. Mondard et al., Proc. Nat. Acad. Sci. 70, pp. 1894–1897 (1973).
Y. Schurch–Rathgeb et al., Nature 273, pp. 308–309 (1978).
J. Guenther et al., The EMBO Journal 4, pp. 1963–1985 (1985).
R. W. Scott et al., J. Biol. Chem. 260, pp. 7029–7033 (1985).
G. E. Davis et al., TINS 1985, pp. 528–532 (1985).
S. Gloor, J. Guenther, D. Monard and H. Nick, J. Guenther and D. Monard, both in Experientia, 42, 631 (1987).
Gloor, S., et al., Cell, vol. 47, 687–693, (1986).
Sommer, Juerg, et al., Biochemistry, 26, 6407 (1987).
Shea, T.B., (1991) "Transient neuritogensis in NB2a/d1 neuroblastoma cells induced by glial–derived protease inhibitors," *Cell. Biol. Intl. Rpts.*, 15:437–443.
Spendlove, R.S., 1995 in: Art to Science. In Tissue and Cell Culture. vol. 14(1), 1995, HyClone Laboratories Newsletter, pp. 1, 2, 5–7.
Gurwitz et al., (1988) "Thrombin modulates and reverses neuroblastoma neurite outgrowth," *Proc. Natl. Acad. Sci. USA*, 85:3440–3444.
Hu et al., (1988) "Expression of the cDNA for mouse beta–nerve growth factor protein in *Escherichia coli*," *Gene*, 70:57–65.
Burton et al., (1992) "Activity and biospecificity of proteolyzed forms and dimeric combinations of recombinant human and murine nerve growth factor," *J. Nuerochem.*, 59:1937–1945.
Hamel et al., (1993) "Neurotrophin gene expression by cell lines derived from human gliomas," *J. Neurosci. Res.*, 34:147–157.
Shea et al., (1992) "Sequential effects of astroglial–derived factors on neurite outgrowth: initiation by protease inhibitors and potentiation by extracellular matrix components." *J. Neurosci. Res.*, 31:309–317.
Gurwitz et al., (1990) "Neurite outgrowth activity of protease nexin–1 on neuroblastoma cells requires thrombin inhibition," *J. Cell. Physiol.*, 142:155–162.
Cunningham et al., (1989) "Proteolytic regulation of neurite outgrowth from neuroblastoma cells by thrombin and protease nexin–1," *J. Cell. Biochem.*, 39:55–64.
Kligman et al., (1987) "Neurite extension factor induces rapid morphological differentiation of mouse meuroblastoma cells in defined medium," *Brain Res.*, 430:296–300.
Mahonen et al., (1985) "Adhesive membrane protein of rat brain enhances neurite outgrowth of neuroblastoma cells," *Eur. J. Cell. Biol.*, 36:91–97.
Meier et al., (1989) "Induction of a glia–derived nexin after lesion of a peripheral nerve," *Nature*, 342:548–550.
Shea, T. B. 1991 Cell Biol. Intl. Rpts. 15(5):437–443.
Spendlove, R. S. 1995 in:Art to Science. In Tissue and Cell Culture. vol. 14(1), 1995, HyClone Laboratories Newsletter, pp. 1, 2, 5, –7.
*Stedtman's Medical Dictionary*, 25th edition, (Hensyl et al., eds.), Williams and Wilkins, Baltimore, MD, pp. 1139, 1140, and 1610.
*Pharmaceutical Sciences*, 1990 Mack Publ. Co., Easton, PA, p. 387.

(List continued on next page.)

*Primary Examiner*—Christopher S. F. Low
*Attorney, Agent, or Firm*—Karl Bozicevic; Carol L. Francis; Fish & Richardson

[57] ABSTRACT

The invention relates to a neurite-promoting factor released by glial cells, to related proteins and fragments thereof retaining their neurite-promoting activity, to DNAs coding for the amino acid sequence of the neurite-promoting factor and fragments thereof, to hybrid vectors containing such DNAs, to hosts transformed with such a hybrid vector, to processes for the preparation of the DNAs, vectors and transformed hosts, to processes for the manufacture of the neurite-promoting factor, related proteins and its fragments, and to their use in the treatment of lesions in the nervous system.

11 Claims, 1 Drawing Sheet

OTHER PUBLICATIONS

*ATCC Catalog of Cell Lines & Hybridomas,* 1988, American Type Culture Collection. Hay et al. (eds.) 1988, Rockville, MD, p. 78.

Stryer, L. 1975. in: *Biochemistry.* W. H. Freman and Co. San Francisco. pp. 336–337.

Scott, et al. 1985. J. Biol. Chem. 260, 7029–7034.

McGrogan et al. 1988 Bio/Technol. 6, 172–177.

Wallace et al. 1980. Nuc. Acids Res. 9, 879–894.

Beaucage et al. 1981 Deoxynucleoside phosphoramidites—a new class of key intermediates for deoxypolynucleotide synthesis. Tet. Ltrs. 22, 1859–1862.

Guenther et al. 1985 A glia–derived neurite–promoting factor with protease inhibitory activity. EMBO J. 4, 1963–1966.

Robson et al. (eds.) 1986 *Introduction to Proteins and Protein Engineering,* Elsevier, New York. pp. 34–39.

Hay et al. (eds.) 1988 *American Type Culture Collection Catalogue of Cell Lines and Hybridomas* Sixth Edition. Rockville, MD p. 239.

Vieira et al. 1982 The pUC plasmids, an M13mp7–derived system for insertion mutagenesis and sequencing with synthetic universal primers Gene 19, 259–268.

Gerhardt et al. 1981 *Manual of Methods for General Bacteriology* Am. Soc. for Microbiol. Washington, D. C. pp. 329–332.

Beck et al. 1995 Nature 373: 339–341.

Henderson, Z. 1996 Progress in Neurobiology 48: 219–254.

Sjostrom et al. 1987 Signal peptide amino acid sequences in *Escherichia coli* contain information related to final protein localization. A multivariate data analysis. EMBO J. 6, 823–831.

Clark–Lewis et al. 1986 Automated chemical synthesis of a protein growth factor for hematopoietic cells, interleukin–3. Science 231, 134–139.

FIGURE 1

METHOD OF TREATING LESIONS IN A NERVOUS SYSTEM

This is a continuation of application Ser. No. 08/192,808, filed Feb. 8, 1994, now abandoned and which is a continuation of application Ser. No. 07/008,819, filed Jan. 30, 1987, now abandoned.

The invention relates to a neurite-promoting factor released by glial cells, to related proteins and fragments thereof retaining their neurite-promoting activity, to DNAs coding for the amino acid sequence of said neurite-promoting factor and fragments thereof, to hybrid vectors containing such DNAs, to hosts transformed with such a hybrid vector, to processes for the preparation of said DNAs, vectors and transformed hosts, to processes for the manufacture of said neurite-promoting factor, related proteins and its fragments, and to their use in the treatment of lesions in the nervous system.

Glial cells are thought to exert crucial regulatory functions during the development or following lesions of the nervous system. Knowledge about the nature of these glia-neurohal interactions requires the identification of macromolecules present in minute amount in the in vivo situation, Cultured rat glioma cells release a macromolecule which promotes neurite extension in neuroblastoma cells. This rat gila-derived neurite-promoting factor (GdNPF) has been purified and characterized [J. Guenther, H. Nick and D. Monard, EMBO J. 4, 1963–1966 (1985)]. It is a protein having an apparent molecular weight of 43,000 which causes both neurite extension and efficient inhibition of serine proteases such as urokinase, tissue plasminogen activator, thrombin and trypsin. The formation of a sodium dodecyl sulfate resistant complex between the proteases and rat GdNPF has been demonstrated by the same authors. Rat GdNPF inhibits the plasminogen activator activity released or associated with rumour cells and interferes with the migration of granule cell neurons taking place during the development of the cerebellum.

Such a neurite-promoting factor and related peptides, which cause neurite extension and inhibit serine proteases, are expected to promote nerve fiber regeneration following lesions in the nervous system and to interfere with the migration of normal and tumour cells. However, therapeutic applications of the, known rat GdNPF to man are severely hampered by the expected antigenicity of rat GdNPF to man. This problem can be surmounted by the use of human GdNPF.

It is an object of the present invention to provide human GdNPF. The problem of industrial synthesis of GdNPF, fragments thereof retaining neurite-promoting activity and GdNPF-related peptides can be solved by the methods of recombinant DNA technology. A further object of the present invention is therefore to provide DNAs coding for GdNPF isolated from natural sources through establishment of a cDNA library of rat glioma cells, human glioma cells and optionally other glial cells, and a method of selection for DNA coding for GdNPF, and to provide DNA mutants and synthetic DNA sequences coding for GdNPF, GdNPF-related peptides or GdNPF fragments retaining neurite-promoting activity. These DNAs are introduced into hybrid vectors. Microorganisms or mammalian cell cultures transformed with such hybrid vectors will express GdNPF or fragments thereof. It is a further object of the present invention to provide such hybrid vectors, transformed hosts, a process of manufacture of GdNPF, GdNPF-related peptides and fragments thereof, pharmaceutical preparations containing GdNPF, GdNPF-related peptides and fragments thereof, and a method for the treatment of lesions in the nervous system with such compounds.

The invention relates to essentially pure human gila-derived neurite-promoting factor (GdNPF), related polypeptides and fragments thereof retaining neurite-promoting activity. These compounds cause both neurite extension and inhibition of serine proteases.

More specifically the invention relates to human GdNPF of the formula

| | |
|---|---|
| $X_1$—Ser—His—Phe—Asn—Pro—Leu—Ser—Leu—Glu—Glu—Leu—Gly—Ser—Asn—Thr—Gly— | 16 (I) |
| Ile—Gln—Val—Phe—Asn—Gln—Ile—Val—Lys—Ser—Arg—Pro—His—Asp—Asn—Ile— | 32 |
| Val—Ile—Ser—Pro—His—Gly—Ile—Ala—Ser—Val—Leu—Gly—Met—Leu—Gln—Leu— | 48 |
| Gly—Ala—Asp—Gly—Arg—Thr—Lys—Lys—Gln—Leu—Ala—Met—Val—Met—Arg—Tyr— | 64 |
| Gly—Val—Asn—Gly—Val—Gly—Lys—Ile—Leu—Lys—Lys—Ile—Asn—Lys—Ala—Ile— | 80 |
| Val—Ser—Lys—Lys—Asn—Lys—Asp—Ile—Val—Thr—Val—Ala—Asn—Ala—Val—Phe— | 96 |
| Val—Lys—Asn—Ala—Ser—Glu—Ile—Glu—Val—Pro—Phe—Val—Thr—Arg—Asn—Lys— | 112 |
| Asp—Val—Phe—Gln—Cys—Glu—Val—Arg—Asn—Val—Asn—Phe—Glu—Asp—Pro—Ala— | 128 |
| Ser—Ala—Cys—Asp—Ser—Ile—Asn—Ala—Trp—Val—Lys—Asn—Glu—Thr—Arg—Asp— | 144 |
| Met—Ile—Asp—Asn—Leu—Leu—Ser—Pro—Asp—Leu—Ile—Asp—Gly—Val—Leu—Thr— | 160 |
| Arg—Leu—Val—Leu—Val—Asn—Ala—Val—Tyr—Phe—Lys—Gly—Leu—Trp—Lys—Ser— | 176 |
| Arg—Phe—Gln—Pro—Glu—Asn—Thr—Lys—Lys—Arg—Thr—Phe—Val—Ala—Ala—Asp— | 192 |
| Gly—Lys—Ser—Tyr—Gln—Val—Pro—Met—Leu—Ala—Gln—Leu—Ser—Val—Phe—Arg— | 208 |
| Cys—Gly—Ser—Thr—Ser—Ala—Pro—Asn—Asp—Leu—Trp—Tyr—Asn—Phe—Ile—Glu— | 224 |
| Leu—Pro—Tyr—His—Gly—Glu—Ser—Ile—Ser—Met—Leu—Ile—Ala—Leu—Pro—Thr— | 240 |
| Glu—Ser—Ser—Thr—Pro—Leu—Ser—Ala—Ile—Ile—Pro—His—Ile—Ser—Thr—Lys— | 256 |
| Thr—Ile—Asp—Ser—Trp—Met—Ser—Ile—Met—Val—Pro—Lys—Arg—Val—Gln—Val— | 272 |

-continued

| | |
|---|---|
| Ile—Leu—Pro—Lys—Phe—Thr—Ala—Val—Ala—Gln—Thr—Asp—Leu—Lys—Glu—Pro— | 288 |
| Leu—Lys—Val—Leu—Gly—Ile—Thr—Asp—Met—Phe—Asp—Ser—Ser—Lys—Ala—Asn— | 304 |
| Phe—Ala—Lys—Ile—Thr—X$_2$—Ser—Glu—Asn—Leu—His—Val—Ser—His—Ile—Leu— | 320 |
| Gln—Lys—Ala—Lys—Ile—Glu—Val—Ser—Glu—Asp—Gly—Thr—Lys—Ala—Ser—Ala— | 336 |
| Ala—Thr—Thr—Ala—Ile—Leu—Ile—Ala—Arg—Ser—Ser—Pro—Pro—Trp—Phe—Ile— | 352 |
| Val—Asp—Arg—Pro—Phe—Leu—Phe—Ile—Arg—His—Asn—Pro—Thr—Gly—Ala— | 368 |
| Val—Leu—Phe—Met—Gly—Gln—Ile—Asn—Lys—Pro | 378, | optionally glycosylated, wherein Cys is optionally in the disulfide form, $X_1$ is hydrogen, acyl, for example formyl or alkanoyl, e.g. palmitoyl, myristoyl or lower alkanoyl, such as acetyl or propionyl, the peptide residue of the formula (II)

or a fragment of the residue of formula II comprising between 1 and 18 amino acids from the carboxyl end, optionally in acylated form, and $X_2$ is Arg or Thr—Gly, to related polypeptides retaining neurite-promoting activity, wherein one or more, especially one, two, three or four, single amino acids in the compound of the formula I are replaced by other amino acids, and to fragments of the compound of formula I comprising at least 10 consecutive amino acids selected from the amino acid chain between the amino acid 29 and amino acid 378 and optionally one or more, e.g. one, two or three other amino acids.

The GdNPF of formula I may be glycosylated or devoid of carbohydrate residues. Typically, a glycosylated GdNPF of formula I contains one or more carbohydrate residues, e.g. N-acetylglucosamine or an oligosaccharide containing N-acetylglucosamine N-glycosidically linked to an asparagine (Asn) residue and/or N-acetylgalactosamine or an oligosaccharide containing N-acetylgalactosamine O-glycosidically linked to a serine (Set) or threonine (Thr) residue.

It is understood that in the GdNPF of formula I the cysteine residues may be in the reduced form as shown or in the oxidized, i.e. disulfide form giving rise to S-S-bridges, preferably intramolecular S-S-bridges between any two Cys residues in the formula I.

Acyl $X_1$ may be any acyl group found in native proteins. Particularly, acyl $X_1$ is lower alkanoyl, e.g. acetyl, or formyl, preferably acetyl.

The peptide residue $X_1$ of the formula II is a signal peptide. The GdNPF as formed in the ribosomes contains the whole peptide residue $X_1$ of formula II. Post-translational processing then cuts off this signal peptide or part of it. The invention relates to the GdNPF of formula I, wherein $X_1$ is the peptide residue of the formula II or fragments of this residue as defined hereinbefore, particularly wherein $X_1$ is the fragment comprising the amino acids −18 to −1, Pro—Ser—Ile—Cys— (−4 to −1), Ser—Ile—Cys— (−3 to −1), Ile—Cys—, or Cys— only. The peptide residue of formula II or its fragments comprising between 1 and 18 amino acids from the carboxyl end may be acylated, e.g. acetylated or formulated, at the N-terminal.

Protease nexin-I was first disclosed in R. W. Scott et al. [J. Biol. Chem. 260, 7029–7034 (1985)]. However, Scott et al. do not describe or recognize the ability of PN-I to treat disorders of the nervous system.

The invention comprises also GdNPF-related polypeptides retaining neurite-promoting activity, e.g. a compound of the formula I, wherein one or more single amine acids are replaced by other amine acids. Such related polypeptides may be formed by spontaneous or chemically-induced mutations at the DNA level or by replacement of amine acids by chemical synthesis. Such related polypeptides comprise also hybrid polypeptides consisting of fused fragments of GdNPF derived from different animal species including human GdNPF.

Fragments of the invention are e.g. large fragments of the compound of formula I, wherein only few amine acids at the N-terminal are missing, for example fragments comprising amine acids 2 to 378, 3 to 378, 4 to 378, 5 to 378, 6 to 378, or 7 to 378, or small fragments of 10 to 50 amine acids comprising amine acids $^{310}$Arg and $^{311}$Ser and/or amine acids $^{345}$Arg and $^{346}$Ser and optionally other amine acids, combinations known to be essential parts of serine protease substrates. Other preferred fragments involve those regions showing considerable hemology with antithrombin-III or αl-antitrypsin, e.g. fragments comprising amine acids selected from the amino acid chain 72 to 96, 134 to 146, 159 to 195, and 314 to 378, and optionally one or more, e.g. one, two or three other amino acids. Particularly preferred are the fragment consisting of 14 amino acids between amino acid 321 and 334, i.e. the fragment of the formula Gln—Lys—Ala—Lys—Ile—Glu—Val—Ser—Glu—Asp—Gly—Thr—Lys—Ala, the fragment consisting of 13 amino acids between amino acids 322 and 334 with an additional histidine residue at the N-terminal; i.e. the fragment of the formula His—Lys—Ala—Lys—Ile—Glu—Val—Ser—Glu—Asp—Gly—Thr—Lys—Ala; the fragment consisting of 10 amino acids between amino acid 345 and 354 with an additional —Ser—Phe residue at the carboxy terminal, i.e. the fragment of the formula Arg—Ser—Ser—Pro—Pro—Trp—Phe—Ile—Val—Asp—Ser—Phe; and the fragment consisting of 14 amino acids between amino acid 175 and 188, i.e. the fragment of the formula Lys—Ser—Arg—Phe—Gln—Pro—Glu—Asn—Thr—Lys—Lys—Arg—Thr—Phe.

The human GdNPF, related peptides and fragments thereof can be prepared by isolation from cells producing the desired compound or by synthesis by condensation reactions.

For example, human GdNPF may be obtained by culturing glioma cells or other glial cells producing it in suitable media, e.g. minimum essential medium, Dulhecco's modified Eagle medium, RPMI 1640 medium and the like, optionally supplemented with whole serum, e.g. fetal calf serum and/or growth-stimulating compounds, mitogens, antibiotics and other supplements. The desired GdNPF is isolated and purified by usual methods such as those discussed hereinbelow.

It is also possible to synthesize human GdNPF, related peptides and particularly fragments thereof by chemical methods, e.g. by condensation reactions as described in M. Bodanszky, Principles of Peptide Synthesis, Springer-Verlag 1984. Fragments are synthesized e.g. by a solid-phase method, wherein a N-protected amino acid is coupled to a suitable resin, the protecting group is removed, a second N-protected amino acid is condensed with the amino group of the first amino acid, the cycle of deprotection/condensation with the next N-protected amino acid is repeated until the peptide residue of the desired composition is complete, and finally this peptide residue is cleaved from the resin and deprotected. Suitable resins, protecting groups, condensation reagents and reaction conditions are well known in the art.

In particular, human GdNPF, related peptides and fragments thereof can be prepared by recombinant DNA technique comprising, for example, culturing a transformed host under conditions which allow expression of the heterologous polypeptide and isolating the desired compound. More specifically, the desired compounds are prepared by a) isolating a DNA coding for GdNPF or a fragment thereof from a cDNA library of glial cells or a genomic DNA library and optionally mutating it, or chemically synthesizing such a DNA,
b) incorporating the DNA into an appropriate expression vector,
c) transferring the obtained hybrid vector into a recipient host,
d) selecting the transformed host from untransformed hosts, e.g. by culturing under conditions under which only the transformed host survives,
e) culturing the transformed host under conditions which allow expression of the heterologous polypeptide, and
f) isolating the human GdNPF, related peptide, or fragment thereof.

The steps involved in the preparation of these peptides by recombinant DNA technique will be discussed in more detail hereinbelow.

For the preparation of human GdNPF, the cDNA library of step a) is preferentially derived from human glioma cells, e.g. from the human glioma cell line LN-340, which has been deposited at the "Collection Nationale de Cultures de Microorganismes", Institut Pasteur, Paris, on Feb. 5, 1986 under the number I-518. A ganomit DNA library of step a) may be prepared from human placenta or human fetal liver cells. For the preparation of related peptides, e.g. rat GdNPF, other glial cells, e.g. rat glioma cells, in particular C6 rat glioma cells, are used to prepare a cDNA library.

The invention relates also to DNAs coding for glia-derived neurite-promoting factor (GdNPF), e.g. DNAs coding for human GdNPF or for rat GdNPF, to mutants thereof, e.g. DNAs wherein one or more, especially one, two, three or four, nucleotides are mutated, to DNAs coding for related polypeptides retaining neurite-promoting activity, and to fragments of such DNA comprising at least 15 nucleotides. It is understood that such DNAs are single-stranded or double-stranded.

In particular, the invention concerns a DNA coding for human GdNPF, of the formula $$Z_1-Y_{13}-Y_3-Y_{18}-Y_9Y_{11}-Y_{15}-Y_{11}-Y_{14}-Y_{11}-Y_{11}-Y_1-Y_{16}-Y_{20}-Y_{17}-Y_{11}-Y_{15}-Y_{16}-Y_{10}-Y_5-Y_{16}-Y_9-Y_{14}-Y_3-Y_{15}-Y_{11}-Y_{16}-Y_{11}-Y_7-Y_7-Y_{11}-Y_8-Y_{16}-Y_3-Y_{17}-Y_8-Y_{10}-Y_6-Y_{20}-Y_{14}-Y_3-Y_6-Y_{10}-Y_{20}-Y_{12}-Y_{16}-Y_2-Y_{15}-Y_6-Y_4-Y_3-Y_{10}-Y_{20}-Y_{10}-Y_{16}-Y_{15}-Y_9-Y_8-Y_{10}-Y_1-Y_{16}-Y_{20}-Y_{11}-Y_8-Y_{13}-Y_{11}-Y_6-Y_{11}-Y_8-Y_1-Y_4-Y_8-Y_2-Y_{17}-Y_{12}-Y_{12}-Y_6-Y_{11}-Y_1-Y_{13}-Y_{20}-Y_{13}-Y_2-Y_{19}-Y_8-Y_{20}-Y_3-Y_8-Y_{20}-Y_8-Y_{12}-Y_{10}-Y_{11}-Y_{12}-Y_{12}-Y_{10}-Y_3-Y_{12}-Y_1-Y_{10}-Y_{20}-Y_{16}-Y_{12}-Y_{12}-Y_3-Y_{12}-Y_4-Y_{10}-Y_{20}-Y_{17}-Y_{20}-Y_1-Y_3-Y_1-Y_{20}-Y_{14}-Y_{20}-Y_{12}-Y_3-Y_1-Y_{16}-Y_7-Y_{10}-Y_7-Y_{20}-Y_{15}-Y_{14}-Y_{20}-Y_{17}-Y_2-Y_3-Y_{12}-Y_4-Y_{20}-Y_{14}-Y_6-Y_5-Y_7-Y_{20}-Y_2-Y_3-Y_{20}-Y_3-Y_{14}-Y_7-Y_4-Y_{15}-Y_1-Y_{16}-Y_1-Y_5-Y_4-Y_{16}-Y_{10}-Y_3-Y_1-Y_{18}-Y_{20}-Y_{12}-Y_3-Y_7-Y_{17}-Y_2-Y_4-Y_{13}-Y_{10}-Y_4-Y_3-Y_{11}-Y_{11}-Y_{16}-Y_{15}-Y_4-Y_{11}-Y_{10}-Y_4-Y_8-Y_{20}-Y_{11}-Y_{17}-Y_2-Y_{11}-Y_{20}-Y_{11}-Y_{20}-Y_3-Y_1-Y_{20}-Y_{19}-Y_{14}-Y_{12}-Y_8-Y_{11}-Y_{18}-Y_{12}-Y_{16}-Y_2-Y_{14}-Y_6-Y_{15}-Y_7-Y_3-Y_{17}-Y_{12}-Y_{12}-Y_2-Y_{17}-Y_{14}-Y_{20}-Y_1-Y_1-Y_4-Y_8-Y_{12}-Y_{12}-Y_{16}-Y_{19}-Y_6-Y_{20}-Y_{15}-Y_{13}-Y_{11}-Y_1-Y_6-Y_{11}-Y_{16}-Y_{20}-Y_{14}-Y_2-Y_5-Y_8-Y_{16}-Y_{17}-Y_{16}-Y_1-Y_{15}-Y_3-Y_4-Y_{11}-Y_{18}-Y_{19}-Y_3-Y_{14}-Y_{10}-Y_7-Y_{11}-Y_{15}-Y_{19}-Y_9-Y_8-Y_7-Y_{16}-Y_{10}-Y_{16}-Y_{13}-Y_{11}-Y_{10}-Y_1-Y_{11}-Y_{15}-Y_{17}-Y_7-Y_{16}-Y_{16}-Y_{17}-Y_{15}-Y_{11}-Y_{16}Y_1-y10-Y_{10}-Y_{15}-Y_9-Y_{10}-Y_{16}-Y_{17}-Y_{12}-Y_{17}-Y_{12}-Y_{17}-Y_{10}-Y_4-Y_{16}-Y_{18}-Y_{13}-Y_{16}-Y_{10}-Y_{13}-Y_{20}-Y_{15}-Y_{12}-Y_2-Y_{20}-Y_6-Y_{20}-Y_{10}-Y_{11}-Y_{15}-Y_{12}-Y_{14}-Y_{17}-Y_1-Y_{20}-Y_1-Y_6-Y_{17}-Y_4-Y_{11}-Y_{12}-Y_7-Y_{15}-Y_{11}-Y_{12}-Y_{20}-Y_{11}-Y_8-Y_{10}-Y_{17}-Y_4-Y_{13}-Y_{14}-Y_4-Y_{16}-Y_{16}-Y_{12}-Y_1-Y_3-Y_{14}-Y_1-Y_{12}-Y_{10}-Y_{17}-Y_{22}-Y_{16}-Y_7-Y_3-Y_{11}-Y_9-Y_{20}-Y_{16}-Y_9-Y_{10}-Y_{11}-Y_6-Y_{12}-Y_1-Y_{12}-Y_{10}-Y_7-Y_{20}-Y_{16}-Y_7-Y_4-Y_8-Y_{17}-Y_{12}-Y_1-Y_{16}-Y_1-Y_1-Y_{17}-Y_{17}-Y_1-Y_{10}-Y_{11}-Y_{10}-Y_1-Y_2-Y_{16}-Y_{16}-Y_{15}-Y_{15}-Y_{18}-Y_{14}-Y_{10}-Y_{20}-Y_4-Y_2-Y_{15}-Y_{14}-Y_{11}Y_{14}-Y_{14}-Y_{10}-Y_2-Y_9-Y_3-Y_{15}-Y_{17}-Y_8-Y_1-Y_{20}-Y_{11}-Y_{14}-Y_{13}-Y_8-Y_6-Y_{10}-Y_3-Y_{12}-Y_{15}-Y_{21}-Z_2$$

(III), wherein $Y_1$ codes for alanine (Ala) and is GCT, GCC, GCA or GCG, $Y_2$ codes for arginine (Arg) and is CGT, CGC, CGA, CGG, AGA or AGG, $Y_3$ codes for asparagine (Asn) and is AAT or AAC, $Y_4$ codes for aspattic acid (Asp) and is GAT or GAC, $Y_5$ codes for cysteine (Cys) and is TGT or TGC, $Y_6$ codes for glutamine (Gln) and is CAA or CAG, $Y_7$ codes for glutamic acid (Glu) and is GAA or GAG, $Y_8$ codes for glycine (Gly) and is GGT, GGC, GGA or GGG, $Y_9$ codes for histidine (His) and is CAT or CAC, $Y_{10}$ codes for isoleucine (Ile) and is ATT, ATC or ATA, $Y_{11}$ codes for leucine (Leu) and is TGA, TTG, CTT, CTC, CTA or CTG, $Y_{12}$ codes for lysine (Lys) and is AAA or AAG, $Y_{13}$ codes for methionine (Met) and is ATG, $Y_{14}$ codes for phenylalanine (Phe) and is TTT or TTC, $Y_{15}$ codes for proline (Pro) and is CCT, CCC, CCA or CCG, $Y_{16}$ codes for serine (Set) and is TCT, TCC, TCA, TCG, AGT or AGC, $Y_{17}$ codes for threonine (Thr) and is ACT, ACC, ACA or ACG, $Y_{18}$ codes for tryptophan (Trp) and is TGG, $Y_{19}$ codes for tyrosine (Tyr) and is TAT or TAC, $Y_{20}$ codes for valine (Val) and is GTT, GTC, GTA or GTG, $Y_{21}$ is a stop codon TAA, TAG or TGA, $Y_{22}$ is $Y_2$ or $Y_{17}$–$Y_8$, $Z_1$ is a flanking DNA residue of 12 nucleotides or more containing a promoter sequence, and $Z_2$ is absent or a flanking DNA residue of one or more nucleotides and $Z_1$ and $Z_2$ are optionally linked, a double-stranded DNA consisting of a DNA of formula III and of a complementary DNA thereto, wherein adenine (A) combines with thymine (T) and vice versa, and guanine (G) combines with cytosine (C) and vice versa, that complementary DNA itself, a mutant thereof, wherein one or more, especially one, two, three or four nucleotides are mutated, and fragments of such DNA comprising at least 15 nucleotides.

Especially, the invention concerns the cDNA coding for human GdNPF, of the formula wherein W is A or ACAG, $X_2$ is Arg or Thr—Gly and $Z_3$ and $Z_4$, independently, are absent or a flanking DNA residue of one or more nucleotides optionally linked, a double-stranded DNA consisting of a DNA of formula IV and of a complementary DNA thereto, that complementary DNA itself, a mutant thereof, wherein one or more, especially one, two, three or four nucleotides are mutated, and fragments of such DNA comprising at least 15 nucleotides.

The invention relates also to a DNA which hybridizes with a DNA of formula IV or with a DNA complementary to the DNA of formula IV.

The invention further concerns the cDNA coding for rat GdNPF, of the formula

```
                                    Met Asn Trp His Leu Pro Leu Phe Leu Leu Ala Ser    -8    (IV)
Z3—CGGTCGTCCTTGGTGGAAGTAACCATGAACTGGCATCTCCCCCTCTTCCTCTTGGCCTCT             60

-1  1
Val Thr Leu Pro Ser Ile Cys Ser His Phe Asn Pro Leu Ser Leu Glu Glu Leu Gly Ser Asn   14
GTGACGCTGCCTTCCATCTGCTCCCACTTCAATCCTCTGTCTCTCGAGGAACTAGGCTCCAAC                 123

Thr Gly Ile Gln Val Phe Asn Gln Ile Val Lys Ser Arg Pro His Asp Asn Ile Val Ile Ser   35
ACGGGGATCCAGGTTTTCAATCAGATTGTGAAGTCGAGGCCTCATGACAACATCGTGATCTCT                 186

Pro His Gly Ile Ala Ser Val Leu Gly Met Leu Gln Leu Gly Ala Asp Gly Arg Thr Lys Lys   56
CCCCATGGGATTGCGTCGGTCCTGGGGATGCTTCAGCTGGGGGCGGACGGCAGGACCAAGAAG                 249

Gln Leu Ala Met Val Met Arg Tyr Gly Val Asn Gly Val Gly Lys Ile Leu Lys Lys Ile Asn   77
CAGCTCGCCATGGTGATGAGATACGGCGTAAATGGAGTTGGTAAAATATTAAAGAAGATCAAC                 312

Lys Ala Ile Val Ser Lys Lys Asn Lys Asp Ile Val Thr Val Ala Asn Ala Val Phe Val Lys   98
AAGGCCATCGTCTCCAAGAAGAATAAAGACATTGTGACAGTGGCTAACGCCGTGTTTGTTAAG                 375

Asn Ala Ser Glu Ile Glu Val Pro Phe Val Thr Arg Asn Lys Asp Val Phe Gln Cys Glu Val  119
AATGCCTCTGAAATTGAAGTGCCTTTTGTTACAAGGAACAAAGATGTGTTCCAGTGTGAGGTC                 438

Arg Asn Val Asn Phe Glu Asp Pro Ala Ser Ala Cys Asp Ser Ile Asn Ala Trp Val Lys Asn  140
CGGAATGTGAACTTTGAGGATCCAGCCTCTGCCTGTGATTCCATCAATGCATGGGTTAAAAAC                 501

Glu Thr Arg Asp Met Ile Asp Asn Leu Leu Ser Pro Asp Leu Ile Asp Gly Val Leu Thr Arg  161
GAAACCAGGGATATGATTGACAATCTGCTGTCCCCAGATCTTATTGATGGTGTGCTCACCAGA                 564

Leu Val Leu Val Asn Ala Val Tyr Phe Lys Gly Leu Trp Lys Ser Arg Phe Gln Pro Glu Asn  182
CTGGTCCTCGTCAACGCAGTGTATTTCAAGGGTCTGTGGAAATCACGGTTCCAACCCGAGAAC                 627

Thr Lys Lys Arg Thr Phe Val Ala Ala Asp Gly Lys Ser Tyr Gln Val Pro Met Leu Ala Gln  203
ACAAAGAAACGCACTTTCGTGGCAGCCGACGGGAAATCCTATCAAGTGCCAATGCTGGCCCAG                 690

Leu Ser Val Phe Arg Cyc Gly Ser Thr Ser Ala Pro Asn Asp Leu Trp Tyr Asn Phe Ile Glu  224
CTCTCCGTGTTCCGGTGTGGGTCGACAAGTGCCCCCAATGATTTATGGTACAACTTCATTGAA                 753

Leu Pro Tyr His Gly Glu Ser Ile Ser Met Leu Ile Ala Leu Pro Thr Glu Ser Ser Thr Pro  245
CTGCCCTACCACGGGGAAAGCATCAGCATGCTGATTGCACTGCCGACTGAGAGCTCCACTCCG                 816

Leu Ser Ala Ile Ile Pro His Ile Ser Thr Lys Thr Ile Asp Ser Trp Met Ser Ile Met Val  266
CTGTCTGCCATCATCCCACACATCAGCACCAAGACCATAGACAGCTGGATGAGCATCATGGTG                 879

Pro Lys Arg Val Gln Val Ile Leu Pro Lys Phe Thr Ala Val Ala Gln Thr Asp Leu Lys Glu  287
CCCAAGAGGGTGCAGGTGATCCTGCCCAAGTTCACAGCTGTAGCACAAACAGATTTGAAGGAG                 942

Pro Leu Lys Val Leu Gly Ile Thr Asp Met Phe Asp Ser Ser Lys Ala Asn Phe Ala Lys Ile  308
CCGCTGAAAGTTCTTGGCATTACTGACATGTTTGATTCATCAAAGGCAAATTTTGCAAAAATA                1005

Thr X2— Ser Glu Asn Leu His Val Ser His Ile Leu Gln Lys Ala Lys Ile Glu Val Ser Glu  329
ACAWGGTCAGAAAACCTCCATGTTTCTCATATCTTGCAAAAAGCAAAAATTGAAGTCAGTGAA                1068

Asp Gly Thr Lys Ala Ser Ala Ala Thr Thr Ala Ile Leu Ile Ala Arg Ser Ser Pro Pro Trp  350
GATGGAACCAAAGCTTCAGCAGCAACAACTGCAATTCTCATTGCAAGATCATCGCCTCCCTGG                1131

Phe Ile Val Asp Arg Pro Phe Leu Phe Phe Ile Arg His Asn Pro Thr Gly Ala Val Leu Phe  371
TTTATAGTAGACAGACCTTTTCTGTTTTTCATCCGACATAATCCTACAGGTGCTGTGTTATTC                1194

Met Gly Gln Ile  Asn Lys Pro
ATGGGGCAGATAAACAAACCCTGAAGAGTATACAAAAGAAACCATGCAAAGCAACGACTACTT               1257

TGC—Z4.
```

```
                                                                      -1  1                    (V)
     Met Asn Trp His Phe Pro Phe Phe Ile Leu Thr Thr Val Thr Leu Ser Ser Val Tyr Ser       1
Z₅—ATGAATTGGCATTTTCCCTTCTTCATCTTGACCACAGTGACTTTATCCTCTGTGTACTCC                           60

Gln Leu Asn Ser Leu Ser Leu Glu Glu Leu Gly Ser Asp Thr Gly Ile Gln Val Phe Asn           21
CAGCTCAACTCTCTGTCACTCGAGGAACTAGGCTCTGACACAGGGATCCAGGTTTTCAAT                             120

Gln Ile Ile Lys Ser Gln Pro His Glu Asn Val Val Ile Ser Pro His Gly Ile Ala Ser           41
CAGATCATCAAATCACAGCCTCATGAGAACGTTGTCATTTCTCCGCACGGGATTGCGTCC                             180

Ile Leu Gly Met Leu Gln Leu Gly Ala Asp Gly Arg Thr Lys Lys Gln Leu Ser Thr Val           61
ATCTTGGGCATGCTGCAGCTGGGGGCTGACGGCAGGACGAAGAAGCAGCTCTCAACGGTG                             240

Met Arg Tyr Asn Val Asn Gly Val Gly Lys Val Leu Lys Lys Ile Asn Lys Ala Ile Val           81
ATGCGATACAATGTGAACGGAGTCGGAAAAGTGCTGAAGAAGATCAACAAGGCTATAGTC                             300

Ser Lys Lys Asn Lys Asp Ile Val Thr Val Ala Asn Ala Val Phe Val Arg Asn Gly Phe          101
TCCAAAAAGAATAAAGACATAGTGACCGTGGCCAATGCTGTGTTTGTCAGGAATGGCTTT                             360

Lys Val Glu Val Pro Phe Ala Ala Arg Asn Lys Glu Val Phe Gln Cys Glu Val Gln Ser          121
AAAGTGGAAGTGCCTTTTGCAGCAAGGAACAAAGAGGTGTTTCAGTGTGAAGTACAGAGT                             420

Val Asn Phe Gln Asp Pro Ala Ser Ala Cys Asp Ala Ile Asn Phe Trp Val Lys Asn Glu          141
GTGAACTTCCAGGACCCGGCCTCTGCTTGTGATGCCATCAATTTTTGGGTCAAAAATGAG                             480

Thr Arg Gly Met Ile Asp Asn Leu Leu Ser Pro Asn Leu Ile Asp Ser Ala Leu Thr Lys          161
ACGAGGGGCATGATTGACAACCTACTTTCCCCAAATCTGATCGATAGTGTCCTTACCAAA                             540

Leu Val Leu Val Asn Ala Val Tyr Phe Lys Gly Leu Trp Lys Ser Arg Phe Gln Pro Glu          181
CTGGTCCTCGTTAACGCAGTGTATTTCAAGGGTTTGTGGAAATCCCGGTTTCAACCTGAG                             600

Asn Thr Lys Lys Arg Thr Phe Val Ala Gly Asp Gly Lys Ser Tyr Gln Val Pro Met Leu          201
AACACGAAGAAACGGACCTTCGTGGCAGGTGATGGAAAATCCTACCAAGTACCCATGCTA                             660

Ala Gln Leu Ser Val Phe Arg Ser Gly Ser Thr Lys Thr Pro Asn Gly Leu Trp Tyr Asn          221
GCCCAGCTCTCCGTGTTCCGCTCTGGGTCTACCAAAACCCCAAATGGCTTATGGTACAAC                             720

Phe Ile Glu Leu Pro Tyr His Gly Glu Ser Ile Ser Met Leu Ile Ala Leu Pro Thr Glu          241
TTCATTGAGCTACCCTACCATGGTGAGAGCATCAGCATGTTGATCGCCCTGCCAACAGAG                             780

Ser Ser Thr Pro Leu Ser Ala Ile Ile Pro His Ile Ser Thr Lys Thr Ile Asn Ser Trp          261
AGCTCCACCCCACTGTCCGCCATCATCCCTCACATCAGTACCAAGACCATCAATAGCTGG                             840

Met Asn Thr Met Val Pro Lys Arg Met Gln Leu Val Leu Pro Lys Phe Thr Ala Leu Ala          281
ATGAACACCATGGTACCCAAGAGGATGCAGCTGGTCCTGCCCAAGTTCACAGCTCTGGCA                             900

Gln Thr Asp Leu Lys Glu Pro Leu Lys Ala Leu Gly Ile Thr Glu Met Phe Glu Pro Ser          301
CAAACAGATCTGAAGGAGCCACTGAAAGCCCTTGGCATTACTGAGATCTTTGAACCGTCA                             960

Lys Ala Asn Phe Ala Lys Ile Thr Arg Ser Glu Ser Leu His Val Ser His Ile Leu Gln          321
AAGGCAAATTTTGCAAAAATAACAAGGTCAGAGAGCCTTCACGTCTCTCACATCTTGCAG                            1020

Lys Ala Lys Ile Glu Val Ser Glu Asp Gly Thr Lys Ala Ala Val Val Thr Thr Ala Ile          341
AAAGCAAAAATTGAAGTCAGCGAAGATGGGACCAAAGCCGCAGTAGTGACAACTGCAATC                            1080

Leu Ile Ala Arg Ser Ser Pro Pro Trp Phe Ile Val Asp Arg Pro Phe Leu Phe Cys Ile          361
CTAATTGCAAGGTCATCGCCTCCCTGGTTTATAGTAGACAGGCCTTTCCTGTTCTGCATC                            1140

Arg His Asn Pro Thr Gly Ala Ile Leu Phe Leu Gly Gln Val Asn Lys Pro
CGACACAATCCCACAGGTGCCATCTTGTTCCTGGGGCAGGTGAACAAGCCCTGA—Z₆,
``` wherein $Z_5$ and $Z_6$, independently, are absent or a flanking DNA residue of one or more nucleotides optionally linked, a double-stranded DNA consisting of a DNA of formula V and of a complementary DNA thereto, that complementary DNA itself, a mutant thereof, wherein one or more, especially one, two, three or four nucleotides are mutated, and fragments of such DNA comprising at least 15 nucleotides.

Furthermore, the invention concerns RNAs coding for a human GdNPF of formula I or for rat GdNPF, mutants thereof, wherein one or more, especially one, two, three or four nucleotides are mutated, and fragments of such RNAs comprising at least 15 nucleotides, in particular a RNA of formula III, wherein the various Y have the meaning given hereinbefore except that RNA residues replace DNA residues and hence uridine (U) replaces deoxy-thymidine (T), especially a RNA of formula IV and a RNA of formula V, wherein U replaces T.

The DNAs coding for GdNPF, mutants thereof, DNAs coding for related polypeptides retaining neurite-promoting activity and fragments of such DNA can be prepared, for example, by culturing a transformed host and isolating the desired DNA therefrom, or by chemical synthesis through nucleotide condensation.

In particular, such DNAs can be prepared, for example, by a) isolating poly(A) messenger RNA (mRNA) from glial cells, optionally enriching mRNA coding for GdNPF or fragments thereof and preparing single-stranded DNA complementary to that mRNA and therefrom double-stranded complementary DNA (ds cDNA), or b) isolating genomic DNA from suitable cells, e.g. placental or fetal liver cells, and selecting the desired DNA using a DNA probe, and c) incorporating ds cDNA of step a) or dsDNA of step b) into an appropriate expression vector, d) transforming an appropriate host with the obtained hybrid vector, e) selecting the transformed host which contains GdNPF DNA or fragments thereof from hosts containing no GdNPF DNA or fragments thereof, and f) isolating the desired DNA.

Polyadenylated messenger RNA is isolated from glial cells by known methods. Such methods involve, for example, homogenizing tissue in the presence of a detergent and a ribonuclease inhibitor, e.g. hepatin, guanidinlum isothiocyanate and mercaptoethanol, centrifuging the homogenate, precipitating mRNA from the supernatant by salt mixtures containing a magnesium salt, e.g. magnesium chloride, extracting the resuspended precipitate with suitable chloroformphenol mixtures, optionally in the presence of detergents and/or cation chelating agents, and precipitating mRNA from the remaining aqueous, salt-containing phase with ethanol, isopropanol or the like. Otherwise, mRNA may be directly isolated by centrifuging in a cesium chloride gradient followed by ethanol precipitation. Preferentially, such precipitated poly(A) mRNA is further purified by chromatographic methods, e.g. affinity chromatography, for example chromatography on oligo(dT) cellulose or on oligo (dU) sepharose.

Glial cells used for the isolation of mRNA may be of different origin. Preferred are glioma cells which can be multiplied in culture, e.g. human glioma cells or rat glioma cells from established cell lines. Particularly preferred are cells from the human glioma cell line LN-340, which has been deposited at the "Collection Nationale de Cultures de Microorganismes", Institut Pasteur, Paris, on Feb. 5, 1986 under the number I-518.

Optionally, the mRNA isolated from glial cell is enriched in mRNA coding for neurite-promoting factor. This can be done, for example, by velocity fractionation or chromatographic fractionation of mRNA, translation of the fractions in suitable cells, e.g. in frog oocytes, or cell-free systems, e.g. reticulocyte extracts or wheat germ extracts, and screening of the obtained polypeptides for neurite-promoting activity or any other property which parallels neurite-promoting activity, e.g. protease inhibitory activity.

The screening of the obtained polypeptides is particularly effective using antibodies, e.g. polyclonal or monoclonal antibodies, in an immunoassay, for example radioimmunoassay, enzyme immunoassay or immunoassay with fluorescent markers. Such immunoassays and the preparation of polyclonal and monoclonal antibodies are well known in the art and are applied accordingly.

The screening can also be carried out using a hybridization probe with mRNA encoding the neurite-promoting factor, avoiding the additional step of translation. Such hybridization probe may be a fully synthetic DNA consisting of at least 17 nucleotides or a DNA or DNA fragment isolated from a natural source or from a genetically engineered microorganism. For example, a plasmid containing a DNA coding for a GdNPF is multiplied in a suitable host, then linearized and the DNA isolated therefrom. After adding a suitable label to such DNA, e.g. a radioactive label, this DNA is used to screen for messenger RNA coding for a related GdNPF. Preferentially, a hybridization probe consisting of radioactively labelled DNA coding for rat GdNPF is used to screen a mRNA library for the presence of mRNA coding for human GdNPF.

The preparation of a single-stranded DNA from a mRNA template is well known in the art, as is the preparation of a double-stranded DNA from a single-stranded DNA. The mkNA template is incubated with a mix of deoxynucleoside triphosphates, optionally a radioactively labelled deoxynucleoside triphosphate (in order to be able to screen the result of the reaction), a primer sequence such as an oligo-dT residue hybridizing with the poly(A) tail of the messenger RNA and a suitable enzyme, e.g. a reverse transcriptase. After degradation of the template mRNA, the complementary DNA (cDNA) is incubated with a mix of deoxynucleoside triphosphates and a suitable enzyme as above to give a double-stranded DNA. Suitable enzymes are a reverse transcriptase, the Klenow fragment of $E.\ coli$ DNA polymerase I or $T_4$ DNA polymerass. Optionally, the single-stranded DNA is first extended with a tail of like deoxynucleotides to allow the use of a primer sequence of complementary like deoxynucleotides, but the formation of dsDNA usually starts on spontaneous hairpin formation. Such dsDNA obtained as a result of hairpin formation is further processed with S1 nuclease which cuts the hairpin.

As an alternative to the preparation of cDNA from mRNA, genomic DNA may be isolated and screened for DNA coding for the desired polypeptide.

Genomic DNA is isolated from suitable tissue,,preferably from human placenta or human fetal liver cells, according to methods known in the art. A genomic DNA library is prepared therefrom by digestion with suitable restriction endonucleases, e.g. AluI and HaeIII, and incorporation into $\lambda$ charon phage, e.g. $\lambda$ charon 4A, following established procedures. The genomic DNA library replicated on nitrocellulose membranes is screened with a DNA probe, e.g. a synthetic DNA probe of at least 17 nucleotides or a cDNA derived from mRNA coding for the desired polypeptide.

The incorporation of dsDNA prepared from mRNA or of genomic origin into an appropriate vector is well known in the art. Preferentially a suitable vector is cut and provided with tails of like deoxynucleosides. The dsDNA to be annealed then has to bear tails of complementary like deoxynucleotides, which is accomplished by incubation in the presence of the corresponding deoxynucleoside triphosphate and an enzyme such as terminal deoxynucleotidyl transferass. Otherwise, the dsDNA may be incorporated into the vector with the aid of linker oligonucleotides or else by blunt end ligation.

The transformation of an appropriate host with the obtained hybrid vector is well known in the art. For example, $E.\ coli$ are conditioned for transformation by incubation in media containing calcium chloride, then treated with the hybrid vector. Transformed hosts are selected by a suitable marker, for example antibiotics resistance marker, e.g. tetracycline or ampicillin resistance.

The selection of the transformed hosts which contain GdNPF DNA or fragments thereof can be done by several methods. For example, plasmid DNA of transformed hosts is isolated and immobilized by usual methods, then hybridized with total mRNA from the glial cells initially used as a template for cDNA. Hybridizing RNA is eluted and translated in vitro as described hereinbefore. The polypeptides obtained on translation are screened for neurite-promoting activity, for protease inhibitory activity, or for immunoreaction with anti-GdNPF antibodies, and the transformed host containing the corresponding DNA selected. Otherwise, total DNA of transformed hosts is hybridized with DNA coding for GdNPF. For example, DNA of transformed hosts expected to code for human GdNPF is hybridized with DNA probes known to code for rat GdNPF.

The preparation of a DNA of the invention may also be performed by means of chemical synthesis. Suitable methods for the synthesis of DNA have been presented in summary form by S. A. Narang [Tetrabedton 39, 3 (1983)]. The known synthesis techniques allow the preparation of polynucleotides towards 40 nucleotides in length, in good yield, high purity and in a relatively short time. Suitably protected nucleotides are linked with one another by the phosphodiester method [K. L. Agarwal et al., Angew. Chem. 84, 489 (1972)] or the even more efficient phosphotriester method [C. B. Reese, Tetrabedton 34, 3143 (1972)], phosphite triester method [R. L. Letsinger et al., J. Am. Chem. Soc. 98, 3655 (1976)] or phosphoramidite method [S. L. Beaucage and M. H. Caruthers, Tetrahedron Letters 22, 1859 (1981)]. Simplification of the synthesis of the oligonucleotides and polynucleotides is made possible by the solid phase method, in which the nucleotide chains are bound to a suitable polymer. Itakura et al. [J. Am. Chem. Soc. 103, 706 (1981)] use trinucleotides instead of individual nucleotides and link them by the phosphotriester method in the solid phase synthesis. A polynucleotide with up to 67 nucleotides can thus be prepared in a short time and with good yields. The actual double-stranded DNA can be built up enzymatically from chemically prepared overlapping oligonucleotides from both DNA strands, which are held together in the correct arrangement by base-pairing and are then chemically linked by the enzyme DNA ligase. Another possibility comprises incubating overlapping single polynucleotide sequences from the two DNA strands in the presence of the four required deoxynucleoside triphosphates with a DNA polymerase, for example DNA polymerase I, the Klenow fragment of polymerase I or $T_4$ DNA polymerase, or with AMV (arian myeloblastosis virus) reverse transcriptase. The two polynucleotide sequences are thereby held together in the correct arrangement by base-pairing and are supplemented with the required nucleotides by the enzyme to give a complete double-stranded DNA [S. A. Narang et al., Anal. Biochem. 121,356 (1982)].

The invention further relates to hybrid vectors comprising a DNA coding for GdNPF, related peptides or fragments thereof operatively linked to an expression control sequence, and to processes for the preparation thereof.

The vector is selected depending on the host cells envisaged for transformation. Examples of suitable hosts ere microorganisms, which are devoid of or poor in restriction enzymes or modification enzymes, such as yeasts, for example *Saccharomyces cerevisiae*, and strains of bacteria, in particular strains of *Escherichia coli*, for example *E. coli* $X_{1776}$, *E. coli* HB 101, *E. coli* W3110, *E. coli* HB101/ LM1035, *E. coli* JA221 or *E. coli* K12 strain 294, *Bacillus subtilis*, *Bacillus stearothermophilus*, *Pseudomonas*, *Haemophilus*, *Streptococcus* and others, and furthermore cells of higher organisms, in particular established human or animal cell lines. The above strains of *E. coli*, for example *E. coli* HB101 and *E. coli* JA221, and furthermore *Saccharomyces cerevisiae* are preferred as the host microorganism.

In principle, all vectors which replicate and express the GdNPF gene according to the invention in the chosen host are suitable. Examples of vectors which are suitable for the expression of the GdNPF in an *E. coli* strain are bacteriophages, for example derivatives of λ bacteriophages, or plasmids, such as, in particular, the plasmid ColE1 and its derivatives, for example pMB9, pSF2124, pBR317 or pBR322. The preferred vectors of the present invention are derived from plasmid pBR322. Suitable vectors contain a complete replicon and a marker gene, which allows selection and identification of the hosts transformed with the expression plasmids on the basis of a phenotypical trait. Suitable marker genes impart to the host, for example, resistance towards heavy metals, antibiotics and the like. Furthermore, preferred vectors of the present invention contain, outside the replicon and marker gene regions, recognition sequences for restriction endonucleases, go that the GdNPF gene and, if appropriate, the expression control sequence can be inserted at these sites. The preferred vectors, the plasmid pBR322 and derived plasmids, e.g. pUC9, contain an intact replicon, marker genes which confer resistance towards tetracycline and ampicillin ($tet^R$ and $amp^R$) and a number of unique recognition sites for restriction endonucleases, for example PstI (cleaves in the $amp^R$ gene, the $tet^R$ gene remains intact), BamHI, HindIII and SalI (all cleave in the $tet^R$ gene, the $amp^R$ gene remains intact), NruI and EcoRI.

Several expression control sequences can be used for regulation of the gene expression. In particular, expression control sequences of highly expressed genes of the host to be transformed are used. In the case of pBR322 as the hybrid vector and *E. coli* as the host microorganism, for example, the expression control sequences (which contain, inter alia, the promoter and the ribosomal binding site) of the lactose operon, tryptophan operon, arabinose operon and the like, the β-lactamase gene, the corresponding sequences of the phage λ N gene or the phage fd-coat protein gene and others, are suitable. Whilst the plasmid pBR322 already contains the promoter of the β-lactamase gene (β-lac gene), the other expression control sequences must be introduced into the plasmid.

Vectors which are suitable for replication and expression in yeast contain a yeast replication start and a selective genetic marker for yeast. Hybrid vectors which contain a yeast replication start, for example chromosomal autonomously replicating segment (ars), are retained extrachromosomally within the yeast cell after the transformation and are replicated autonomously. Furthermore, hybrid vectors which contain sequences homologous to the yeast 2μ plasmid DNA can be used. Such hybrid vectors will get integrated by recombination into 2μ plasmids already existing within the cell, or replicate autonomously. 2μ sequences are particularly suitable for plasmids with a high transformation frequency and permit high copy numbers. The preferred yeast vector of the present invention is the plasmid pJDB207.

Suitable marker genes for yeasts are, in particular, those which impart antibiotic resistance to the host or, in the case of auxotrophic yeast mutants, genes which complement host lesions. Corresponding genes impart, for example, resistance towards the antibiotic cycloheximide or provide for protrophy in an auxotrophic yeast mutant, for example the URA3, LEU2, HIS3 or, in particular, TRP1 gene. Yeast hybrid vectors furthermore preferably contain a replication start and a marker gene for a bacterial host, in particular *E. coli*, so that the construction and cloning of the hybrid vectors and their intermediates can take place in a bacterial host.

Expression control sequences which are suitable for expression in yeast are, for example, those of highly expressed yeast genes. Thus, the promoters of the TRP1 gene, the ADHI or ADHII gene, acid phosphatase (PH03 or PH05) gene, isocytochrome gene or a promoter involved with the glycolytic pathway, such as the promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used. Preferred vectors of the present invention contain promoters with transcriptional control, e.g. the promoters of the PH05, ADHII and GAPDH genes, which can be turned on or off by variation of the growth conditions. For example, the PH05 promoter can be repressed or derepressed solely by increasing or decreasing the concentration of inorganic phosphate in the medium.

Vectors suitable for replication and expression in mammalian cells are preferably provided with DNA from vital origin, e.g. from simian virus 40 (SV40), Rous sarcoma virus (RSV), adenovirus 2, bovine papilloma virus (BPV), papovavirus BK mutant (BKV), or mouse or h6man cytomegalovirus (CMV). Preferably, such vectors contain an origin of replication and an antibiotics resistance gene for propagation in *E. coli* together with an eukaryotic transcription regulatory sequence. In particular, such so-called shuttle vectors may be constructed from a pBR322 *E. coli* plasmid and SV40 and/or CMV enhancer and promoter regions. For example, the plasmid may contain the enhancer unit of the mouse or human cytomegalovirus major immediate-early gene, the SV40 enhancer combined with the human α-globin promoter, and/or in addition inducible promoters, such as the ones derived from the heat shock or metallothionein genes. Further it is also possible to utilize promoter or control sequences which are normally associated with the desired gene sequence. An origin of replication may be provided either by construction of the vector to include an exogeneous origin, such as derived from SV40, other viral source or provided by the host cell chromosomal replication mechanism. If the vector is integrated into the host cell chromosome, the latter method is often more efficient.

In a preferred embodiment, the present invention relates to hybrid vectors capable of replication and phenotypical selection in a host strain comprising a promoter and a DNA encoding the GdNPF, related peptide or fragment thereof, said DNA being positioned together with transcription start and termination signals as well as translation start and stop signals in said hybrid vector under the control of said promoter such that in a transformed host it is expressed to produce the polypeptide.

The invention also relates to a process for the preparation of a transformed host, which comprises transforming a host with an expression vector containing a DNA of the invention regulated by an expression control sequence, and to the transformed hosts themselves.

Examples of suitable hosts are the above-mentioned microorganisms, such as strains of *Saccharomyces cerevisiae, Bacillus subtilis* and *Escherichia coli*. The transformation with the expression plasmids according to the invention is carried out, for example, as described in the literature, thus for *S. cerevisiae* [A. Hinnen et al., Proc. Natl. Acad. Sci. USA 75, 1929 (1978)], *B. subtilis* [Anagnostopoulos et al., J. Bacteriol. 81,741 (1961)] and *E. coli* [M. Mandel et al., J. Mol. Biol. 53, 159 (1970)].

Accordingly, the transformation procedure of *E. coli* cells includes $Ca^{2+}$-pretreatment of the cells so as to allow DNA uptake, and incubation with the hybrid vector. The cells are transferred to a selective growth medium which allows separation of the transformed cells from the parent cells. Cells which do not contain the vector will not survive in such a medium. The transformation of yeast comprises, for example, the steps of (1) enzymatic removal of the yeast cell wall by means of glucosidases, (2) treatment of the obtained spheroplasts with the vector in the presence of polyethylene glycol and $Ca^{2+}$-ions and (3) regeneration of the cell wall by embedding the spheroplasts into agar. Preferably, the regeneration agar is prepared in a way to allow regeneration and selection of the transformed cells at the same time.

Further examples of suitable hosts are mammalian cells, e.g. COS-7 cells, Bowes melanoma cells, chinese hamster ovary (CHO) cells or embryonic lung cells L-132. The vectors are introduced into mammalian cells by transfection in the prescence of helper compounds, e.g. diethylaminoethyldextran, dimethyl sulfoxide, glycerol, polyethylene glycol or the like, or as co-precipitates of vector DNA and calcium phosphate. Further suitable methods include direct microinjection of vector DNA into the cell nucleus and electroporation, i.e. introduction of DNA by a short electric pulse increasing the permeability of cell membranes. The subsequent selection of transfected cells can be done using a selection marker which is either covalently integrated into the expression vector or added as a separate entity. Selection markers include genes which confer resistance to antibiotics, e.g. G-418 (neomycin) or hygromycin, or genes which complement a genetic lesion of the host cell such as the absence of thymidine kinase or hypoxanthine phosphoribosyl transferass.

The transformed host cells are cultured by methods known in the art in a liquid medium containing assimilable sources of carbon, nitrogen and inorganic salts.

Various sources of carbon can be used for culture of the transformed hosts according to the invention. Examples of preferred sources of carbon are assimilable carbohydrates, such as glucose, maltose, mannitol or lactose, or an acetate, which can be used either by itself or in suitable mixtures. Examples of suitable sources of nitrogen are amino acids, such as casaminoacids, peptides and proteins and their degradation products, such as tryprone, peptone or meat extracts; and furthermore yeast extracts, malt extract and also ammonium salts, for example ammonium chloride, sulfate or nitrate, which can be used either by themselves or in suitable mixtures. Inorganic salts which can also be used are, for example, sulfates, chlorides, phosphates and carbonates of sodium, potassium, magnesium and calcium.

The medium furthermore contains, for example, growth-promoting substances, such as trace elements, for example iron, zinc, manganese and the like, and preferably substances which exert a selection pressure and prevent the growth of cells which have lost the expression plasmid. Thus, for example, ampicillin is added to the medium if the expression plasmid contains an amp gens. Such an addition of antibiotic substances also has the effect that contaminating antibiotic-sensitive microorganisms are destroyed. If a yeast strain which is auxotrophic in, for example, an essential amino acid, is used as the host microorganism, the plasmid preferably contains a gens coding for an enzyme which complements the host defect. Cultivation of the yeast strain is performed in a minimal medium deficient in said amino acid.

Vertebrate cells are grown under tissue culture conditions using commercially available media optionally supplemented with growth-promoting substances and/or mammal sera. The cells are grown either attached to a solid support, e.g. a microcarrier or porous glass fibres, or free-floating in appropriate culture vessels.

Culturing is effected by processes which are known in the art. The culture conditions, such as temperature, pH value of the medium and fermentation time, are chosen so that a maximum titre of the polypeptide of the invention is obtained. Thus, an *E. coli* or yeast strain is preferably cultured under aerobic conditions by submerged culture with shaking or stirring at a temperature of about 20 to 40° C., preferably about 30° C., and a pH value of 4 to 8, preferably at about pH 7, for about 4 to 30 hours, preferably until maximum yields of the polypeptide of the invention are reached.

When the cell density has reached a sufficient value, the glial cells are harvested and the polypeptide is isolated. If the polypeptide is fused with a suitable signal peptide sequence, it is excreted by the cell directly into the supernatant. Otherwise, the cells have to be destroyed, for example by treatment with a detergent, such as SDS, NP-40, TRITON™ or deoxycholic acid, or lysed with lysozyme, a similarly acting enzyme or with ultra-sound. If yeast is used as host microorganism the cell wall may be removed by enzymatic digestion with a glucosidase. Alternatively or additionally, mechanical forces, such as shearing forces (for example X-press, French press, Dyno mill) or shaking with glass beads or aluminium oxide, or alternating freezing, for example in liquid nitrogen, and thawing, for example to 30° to 40° C., can be used to break the cells.

The cell supernatant or the solution obtained after centrifugation of the mixture obtained on breaking the cells, which contains proteins, nucleic acids and other cell constituents, is enriched in proteins, including the polypeptides of the invention, in a manner which is known per se. Thus, for example, most of the non-protein constituents are removed by polyethyleneimine treatment and the proteins, including the polypeptides of the invention, are precipitated, for example, by saturation of the solution with ammonium sulfate or with other salts. Otherwise, the cell supernatant or lysate may be directly pro-purified using chromatographic methods. Further purification steps include, for example, ultrafiltration, diafiltration, gel electrophoresis, chromatographic processes, such as ion exchange chromatography, size exclusion chromatography, high pressure liquid chromatography (HPLC), reversed phase HPLC, fast polypeptide liquid chromatography (FPLC) and the like, separation of the constituents of the mixture according to molecular size by means of a suitable gel filtration column, dialysis, affinity chromatography, for example affinity chromatography using antibodies, especially monoclonal antibodies, and other processes known in the art.

The invention concerns furthermore GdNPF, related peptides and fragments thereof, whenever prepared according to the methods of the present invention.

The invention concerns especially the hybrid vectors, the transformed host cells, human GdNPF and the process for the preparation thereof as described in the Examples.

The neurite-promoting and serine protease-inhibiting properties of GdNPF, related peptides and fragments thereof according to the invention make these polypeptides useful for promoting nerve fiber regeneration following lesions in the nervous system, preferably in the form of pharmaceutical preparations that contain a therapeutically effective amount of the active ingredient optionally together or in admixture with inorganic or organic, solid or liquid, pharmaceutically acceptable carriers which are suitable preferably for parenteral administration.

Parenteral formulations are especially injectable fluids that are effective in various manners, such as intravenously, intramuscularly, intraperitoneally, intranasally, intradermally or subcutaneously. Such fluids are preferably isotonic aqueous solutions or suspensions which can be prepared before use, for example from lyophilized preparations which contain the active ingredient alone or together with a pharmaceutically acceptable carrier. The pharmaceutical preparations may be sterilized and/or contain adjuncts, for example preservatives, stabilizers, wetting agents and/or emulsifiers, solubilizers, salts for regulating the osmotic pressure and/or buffers. The present pharmaceutical preparations, which may, if desired, contain further pharmacologically valuable substances, are produced in a manner known per se, for example by means of conventional dissolving or lyophtlizing processes, and contain from approximately 0.1% to 100%, especially from approximately 1% to approximately 50%, and in the case of lyophilisates up to 100%, of the active ingredient.

The invention also concerns a method for producing a pharmaceutical preparation, characterized in that a pharmacologically active compound of the present invention is admixed with a pharmaceutically acceptable carrier.

The particular mode of administration and the dosage will be selected by the attending physician taking into account the particulars of the patient, the disease and the disease state involved. For instance, lesions of the nervous system are usually treated by daily or twice daily doses over a few days to a few weeks of 0.001 to 1 mg per kg body weight.

The following Examples serve to illustrate the present invention but should not be construed as a limitation thereof.

The abbreviations used in the Examples have the following meanings:

bp base pairs
BSA bovine serum albumin
cDNA complementary DNA
cpm counts per min (radioactive decay)
dA 2'-deoxyadenosine
dATP 2'-deoxyadenosine triphosphate
dC 2'-deoxycytidine
dCTP 2'-deoxycytidine triphosphate
dG 2'-deoxyguanosine
dGTP 2'-deoxyguanosine triphosphate
DMEM Dulbecco's modified Eagle's medium
DNA deoxyribonucleic acid
dNTP mixture of dATP, dCTP, dGTP and dTTP
dpm desintegrations per min (radioactive decay)
ds DNA double-stranded DNA
dT 2'-deoxythymidine
DTT 1,4-dithiothreitol
dTTP 2'-deoxythymidine triphosphate
EDTA ethylenediamine-tetraacetic acid
FCS fetal calf serum
GdNPF gila-derived neurite promoting factor
Hepes N-2-hydroxyethylpiperazine-N'-2-ethanesulfonic acid
mRNA messenger RNA
PBS phosphate buffered physiological saline
Pipes piperazine-N,N'-bis(2-ethanesulfonic acid)
PMSF phenylmethylsulfonyl fluoride
RNA ribonucleic acid
rpm revolutions per min
SDS sodium dodecyl sulfate
TFA trifluoroacetic acid
Tris tris(hydroxymethyl)aminomethane
tRNA transfer RNA The following buffer solutions and media are used:
elution buffer 10 mM Tris-HCl, pH 7.5, 1 mM EDTA, 0.2% SDS.
immunobuffer 50 mM Tris-HCl, pH 7.5, 1 mM EDTA, 150 mM NaCl, 0.1% Tween-20™.
Laemmli sample buffer 62.5 mM Tris-HCl, pH 6.8, 2% SDS, 10% glycerol, 5% 2-mercaptoethanol, 0.001% bromophenol blue.

LB-broth 1% BACTO™tryptone (Difco), 0.5% Bacto™ yeast extract (Difco), 170 mM NaCl, adjusted to pH 7.5 with NaOH.

RVT buffer 200 mM Tris-HCl, pH 8.3 at 42° C., 20 mM $MgCl_2$, 280 mM KCl, 20 mM DTT.

SSC buffer 15 mM sodium citrate, 150 mM NaCl, adjusted to pH 7.0 with NaOH.

TBE buffer 89 mM Tris (TRIZMA® base), 89 mM boric acid, 1 mM EDTA.

TNE buffer 10 mM Tris-HCl, pH 8.0, 1 mM EDTA, 0.1 M NaCl.

wash buffer 10 mM Tris-HCl, pH 7.5, 1 mM EDTA, 0.5 M NaCl, 0.2% SDS.

EXAMPLE 1

Isolation of mRNA from rat C6 glima cells

Rat C6 glioma cells (ATCC No. CCL 107) are grown in 10 cm tissue culture dishes with 15 ml Dulbecco Modified Eagle Medium (Gibco) supplemented with 10% fetal calf serum. 120 confluent dishes (about $2.5 \times 10^7$ rat glioma cells per dish) are used to enrich mRNA as described by R. D. Palmiter [Biochemistry 13, 3606–3615 (1974)]. The mRNA fraction obtained by magnesium precipitation is further purified on oligo(dT) cellulose according to a method of M. Edmonds et al. [Proc. Natl. Acad. Sci. USA68, 1336–1340 (1971)].

EXAMPLE 2

Enriching mRNA for rat GdNPF

600 µg poly(A) RNA from Example 1 (1 µg/µl) are heated for 5 min at 70° C., quickly chilled in ice water and loaded onto a 5–20% linear sucrose gradient in 10 mM Hepes pH 7.5/1 mM EDTA/100 mM NaCl and centrifuged for 23 h at 20000 rpm in a SW 27 rotor at 20° C. 20 fractions are collected and precipitated with ethanol at –20° C. overnight. The mRNA is centrifuged for 20 min at 15000 rpm in a SS-34 rotor, washed once in 75% ethanol and finally dissolved in water at a concentration of 1 µg/µl.

Individual fractions are assayed by injection into frog oocytes in the following way: 50 nl of each mRNA fraction tested is injected into I oocyte. Groups of 3 eggs containing the same mRNA are incubated in 100 µl Barth solution at 22° C. for 24 h. The incubation medium is removed and assayed for protease inhibitory activity (which parallels GdNPF activity) in the casein degradation assay described by J. Guenther et al. [EMBO J. 4, 1963–1966 (1985)]. Briefly, a mixture of milk powder suspension, human urokinase, purified human plasminogen and the solution to be tested is incubated in a suitable buffer mixture, and the caseinolysis monitored by measuring the decrease in turbidity at 405 nm. The following results are obtained:

| Fraction no. | % Inhibition of urokinase |
| --- | --- |
| 1 | not tested |
| 2 | not tested |
| 3 | not tested |
| 4 | 5 |
| 5 | not tested |
| 6 | 5 |
| 7 | not tested |
| 8 | 4 |
| 9 | not tested |
| 10 | 3 |
| 11 | 35 |
| 12 | 29 |
| 13 | 75 |
| 14 | 57 |
| 15 | 38 |
| 16 | 12 |
| 17 | not tested |
| 18 | 6 |
| 19 | not tested |
| 20 | 5 |

The fractions 13 and 14 are pooled and used for cDNA synthesis (Example 3).

EXAMPLE 3

Preparation of ds cDNA coding for rat GdNPF

Enriched mRNA coding for rat GdNPF of Example 2 is used as a template to prepare double-stranded DNA (ds DNA) essentially as described in the Maniatis handbook [T. Maniatis, E. F. Fritsch and J. Sambrook, "Molecular Cloning, a Laboratory Manual", Cold Spring Harbor Laboratory, 1982].

3.1 First strand synthesis: 100 µl reaction mixture containing mM Tris-HCl, pH 8.3 (at 42° C.), 70 mM KCl, 10 mM $MgCl_2$, 1 mM DTT, mM of each dGTP, dCTP and dTTP, 0.4 mM dATP, 50 µCi $\alpha$-$^{32}$P-dATP (Amersham, 3000 Ci/mmol), 50 µg/ml oligo-dT (P-L Biochemicals), 100 µg/ml mRNA (Example 2) and 50 units of arian myeloblastosis virus (AMV) reverse transcriptase (Stehelin, Basel, Switzerland) are incubated for 60 min at 42° C. The reaction is terminated by adjusting the solution to 10 mM EDTA. The mixture is hydrolyzed for min at 52° C. by adding 1 M NaOH to 0.2 M final concentration. After neutralization with 1M Tris-HCl, pH 8.0, and 1 M HCl, the reaction mixture is extracted with phenol/chloroform. The organic phase is back-extracted once with 10 mM Tris-HCl, pH 8.0/1 mM EDTA/100 mM NaCl. The pooled aqueous phases are applied on a SEPHADEX® G-50 column. 100 µl fractions are collected and radio-activity monitored by Cerenkov counting [P. W. J. Rigby etal., J. Mol. Biol. 113, 237–251 (1977)]. cDNA containing fractions are pooled and precipitated with ethanol. The yield of single-stranded cDNA is 4.6 µg. The size of the cDNA is 700–2000 nucleotides in length, as determined from its electrophoretic mobility in a 2% alkaline agarose gel in 30 mM NaOH/1 mM EDTA.

3.2. Second strand synthesis and S 1 digestion: The obtained cDNA is incubated in 100 µl final volume of 100 mM Hepes, pH 6.9, 10 mM $MgCl_2$, 2.5 mM DTT, 70 mM KCl, 0.5 mM of each dNTP, 5.8 µCi $^3$H-dGTP, and 32 units of DNA polymerase (Klenow fragment, Boehringer Mannheim) for 150 min at 20° C. 16 units of the enzyme are added and the incubation continued for 60 min at 37° C. The reaction is terminated by adding EDTA to 10 mM . The mixture is extracted with phenol/chloroform and precipitated with ethanol. The resulting DNA is treated in a 100 µl incubation mixture containing 250 mM NaCl, 50 mM sodium acetate pH 4.5, 1 mM $ZnSO_4$, and 500 units/ml of S 1 endonuclease (Boehringer Mannhelm) at 37° C. for 30 min. The reaction is stopped by adding EDTA to 10 mM . After adding 1 M Tris-HCl, pH 8.0 to 100 mM , the reaction is extracted with phenol/chloroform. The cDNA is precipitated with ethanol at –70° C. for 30 min. After centrifugation, the obtained ds cDNA is dissolved in 20 µl of a solution of 50 mM Tris-HCl pH 7.4, 7 mM $MgCl_2$, 1 mM DDT, 1 mM of each dNTP, and 1.5 units of the Klenow fragment. The reaction is incubated 30 min at 22° C. and then stopped by adding EDTA to 10 mM. After extraction and passing through a SEPHADEX® CL-4B column in 10 mM Tris-HCl, pH 7.5/1 mM EDTA/300 mM NaCl, aliquots of cDNA containing fractions are assayed on a 2% agarose gel. Fractions with molecules>600 bp are pooled, precipitated with ethanol and dissolved in 10 mM Tris-HCl pH 7.5/1 mM EDTA. 0.6 µg ds cDNA are obtained.

EXAMPLE 4

Preparation of a vector containing ds cDNA coding for rat GdNPF from plasmid pBR322 and transformation of E. coli HB 101 therewith 4.1. Preparation of ds cDNA with poly(dC) tails: 540 ng ds cDNA of Example 3 are incubated in 100 µl solution containing 200 mM potassium cacodylate, pH 6.9, 1 mM $CoCl_2$, 260 pmol $^3$H-dCTP, and 6 units of terminal deoxynucleotidyl transferase (P-L Biochemicals) for 5 min at 37° C. To stop the reaction, EDTA is added to 10 mM. The mixture is extracted with phenol/chloroform, and the DNA precipitated with ethanol. dC-tailed cDNA is stored at –20° at 10 ng/µl.

4.2. Annealing of cut pBR322 with poly(dG) tails to ds cDNA with poly(dC) tails and transformation of E. coli with the obtained vector: A mixture of 33 ng dC-tailed ds cDNA from Example 4.1 and 170 ng dG-tailed pBR322 (cut with Pst I, Boehringer Mannheim) in 200 µl 10 mM Tris-HCl, pH 7.5/100 mM NaCl/1 mM EDTA is incubated 5 min at 65° C., 60 min at 55° C. and then cooled to 22° C. in a water bath. 40 µl of this annealing mixture are added to 200 µl of competent E. coli cells strain HB 101, which have been prepared for transformation as described in the Maniatis handbook. The mixture is kept on ice for 30 min and heated to 42° for 2 min, then treated with 1 ml of LB-broth and incubated at 37° C. for 30 min. The mixture (200 µl per plate) is spread on 8 cm agar plates containing LB-broth and 20 Bg/ml tetracycline. The plates are incubated at 37° C. for 16 h. About 5000 tetracycline resistent colonies are obtained.

EXAMPLE 5

Identification of clones containing DNA coding for rat GdNPF by hybridization selected translation 5.1. Hybridization: Individual colonies of Example 4 are grown to saturation in 200 µl LB-broth containing 20 µg/ml tetracycline. To obtain pools of 48 colonies, 50 µl of each preculture are pipetted into 100 ml LB-broth containing 20 µg/ml tetracycline. The pools are grown overnight. The DNA is isolated using the alkaline lysis method as described in the Maniatis handbook. The plasmid DNA is linearized with EcoRI, extracted and dissolved in 10 mM Tris-HCl, pH 7.5/1 mM EDTA at a concentration of 0.1 µg/µl. 100 µl of the solution are pipetted onto untreated Gene Screen™ filters (New England Nuclear, 1 cm) in portions of 20 µl and dried between each step. The filters are put 4 times for 1 min on 3 MM™ paper (Whatman), which is soaked in 0.5 M NaOH/1.5 M NaCl. This procedure is repeated on B MM™ paper soaked in 2 M Tris-HCl pH 7.4/double-concentrated SSC buffer, and finally on 3 MM™ paper soaked only in double-concentrated SSC buffer. The filters are then gently agitated in double-concentrated SSC buffer and baked in a vacuum stove for 2 h at 80° C. Before use the filters are put in boiling water for 1 min. Total RNA from rat C6 glioma cells (Example 1) is dissolved in 30% formamide/20 mM Pipes, pH 7.5/500 mM NaCl/2 mM EDTA/0.4% SDS at a concentration of 2–3 mg/ml. 130 µl of this solution per filter is used for hybridization for 17 h at 42° C. with gentle agitation. The filters are washed 10 times in SSC buffer/ 0.1% SDS at 60° C. and once in 5 mM Tris-HCl, pH 7.5/1 mM EDTA at 60° C. The hybridized RNA is eluted from the filters by two cycles of boiling in 200 µl 5 mM KCl/10 µg/ml tRNA (Boehringer Mannheim, phenol extracted) followed by quick freezing in dry ice-ethanol. After thawing, the eluates are pooled and the RNA precipitated with ethanol at –20° C. overnight. The precipitate is centrifuged and washed in 75% ethanol. The poly(A) RNA obtained from each pool is dissolved in 4 µl water and used for in vitro translation and immunoprecipitation with anti-GdNPF antibodies.

5.2. In vitro translation in the rabbit reticulocyte lysate: Rabbit reticulocyte lysate (Amersham, N.90) is diluted with $^{35}$S-methionine (Amersham, 1000 Ci/mmol) and poly(A) RNA of Example 5.1. on ice to give final concentrations of lysate 70%, $^{35}$S-methionine 2 µCi/µl, and RNA 4 µg/ml. The mixture is incubated at 30° C. for 1 h. 1 µl aliquots are removed at 0 and 60 min respectively, spotted on GF/C filters (Whatman) and used for trichloroacetic acid precipitation according to the Maniatis handbook. For gel electrophoresis 2–4 µl lysate mixture are diluted with 20 µl Laemmli sample buffer, boiled for 2 min and analyzed on a 10% acrylamide gel [U.K. Laemmli, Nature 227, 680 (1970)]. The gels are run at 30–40 mA constant current for 3–4 h. After fixation the gels are treated 30 min with a fluorographic solution (ENLIGHTNING™, New England Nuclear) dried and exposed to preflashed Kodak X-5 films overnight at room temperature.

5.3. Preparation of polyclonal antibodies specific for rat GdNPF: Rabbits are immunized by subcutaneous and intramuscular injection of about 50 µg of purified rat GdNPF [J. Guenther et al., EMBO J. 4, 1963–1966 (1985)] in complete Freund adjuvant (Sigma). Booster injections with about 50 µg of purified rat GdNPF are given in incomplete Freund adjuvant at 4 weeks intervals. Serum is collected 10 days after each booster injection and tested for anti-GdNPF antibodies using the immunodot procedure of R. Hawkes et al. [Anal. Blochem. 119, 142–147 (1982)]. Positive sera are obtained following the second booster injection. The immunoglobulins of positive sera are enriched and purified using standard Protein A-EPHAROSE® CL-4B (Pharmacia) chromatography according to H. Hjelm et al. [FEBS Letters 28, 73–76 (1972)].

5.4. Immunoprecipitation of rat GdNPF synthesized by in vitro translation: 15 µl of the incubated in vitro lysate mixture of Example 5.2. is mixed with 10 µg anti-GdNPF antibodies of Example 5.3. in 150 µl of immunobuffer containing 1 mM PMSF. The mixture is incubated in a siliconized Eppendorf tube for 17 h at 4° C. Protein A-EPHAROSE® CL-4B (Pharmacia) is freshly prepared by swelling the dry powder 2–3 h in PBS, washing it 3 times in immunobuffer containing 2 mg/ml BSA (Pentax, fraction V) and 2 times in the same buffer without BSA. The sepharose is diluted 1:2 with immunobuffer, 15 µl of it added to the Eppendorf tubes containing the lysate mixture and the polyclonal antibodies, and the suspension gently agitated for 60 min. at room temperature. The sepharose is washed 3 times with immunobuffer containing 0.5–1% TWEEN-20™ (polyoxyethylene (20)-sorbitanemo. After the final wash 20 µl Laemmli sample buffer are pipetted to the dry sepharose pellet. The suspension is incubated 10 min at room temperature and finally boiled for 4 min. After cooling in ice and centrifugation, 20 µl of the supernatant are loaded on a 10% polyacrylamide gel. The gel electrophoresis is run and developed as described above in Example 5.2.

Out of the pools of 48 colonies (Example 5.1), one is positive. The 48 colonies of this one pool are combined to 6 new pools of 8 colonies, and treated alike. Finally, a single colony is identified which gives a positive immunoprecipitation after translation. The clone is expanded in LB-broth containing 20 µg/ml tetracyline.

5.5. Sequencing of rat GdNPF cDNA: The cDNA of the positive clone of Example 5.4 is sequenced using the general method of Sanger. 1.5 µg of the recombinant plasmid derived from pBR322 (Example 4.2) in 9 µl water are mixed with 1 µl (0.5 pmoles) of a primer complementary to the pBR322 derived vector just in front of the Pst 1 endonuclease cleavage site. The DNA is denatured by heating for 3 min in boiling water, frozen for 1 min in dry ice/ethanol, thawed at room temperature and mixed with 1 µl 100 mM Tris-HCl pH 8.3/50 mM $MgCl_2$. The annealing mixture is incubated for 30 min at 37° C. The sequencing reaction is performed as described in the Amersham sequencing manual (M13 cloning and sequencing handbook, Amersham). The sequence found is depicted in formula V.

EXAMPLE 6

Cloning of human GdNPF cDNA 6.1. Human glioma cells: Five human glioma cell lines established by Drs. E. H. Macintyre and N. de Tribolet [J. P. Perkins et al., Life Sciences 10, 1069–1080 (1971), B. de Muralt et al., Eur. J. Cancer Clin. Oncol. 21,207–216 (1985)] are analyzed by Northern blot for the presence of mRNA hybridizing with a DNA probe labelled with $^{32}P$ by in vitro nick translation of the positive rat GdNPF cDNA clone of Example 5. 10 µg of total cytoplasmic RNA are used per lane. Hybridisation is done for 15 h at 42° C. using $1\times10^6$ cpm of the nick translated probe per ml. The filters are washed four times for 5 min in 30 mM sodium citrate, pH 7.0/300 mM NaCl/0.1% SDS at room temperature and two times for 15 min in 1.5 mM sodium citrate, pH 7.0/15 mM NaCl/0.1% SDS at 60° C. Cell line LN-340, which has been deposited at the "Collection Nationale de Cultures de Microorganismes", Institut Pasteur, Paris, on Feb. 5, 1986 under the number 1–518, gives strong hybridization and is grown to confluency in 40 10 cm tissue culture dishes.

6.2. Isolation of mRNA: A one ml pellet of human glioma cells LN-340 containing approximately $10^8$ cells is dissolved in 6 ml of a filtered solution prepared from 100 g of guanidinium thiocyanate, 100 ml of $H_2O$, 10.6 ml 1 M Tris-HCl, pH 7.5., 4.2 ml 0.5 M EDTA, 21.2 ml 20% N-laurylsarcosine and 2.1 ml of 2-mercaptoethanol. After vigorous shaking 2.7 g of baked CsCl are added and the solution is layered over a 2 ml cushion of 5.7 M CsCl in 0.1 M EDTA, pH 7.5 in a 12 ml centrifuge tube. The tube is filled up with $H_2O$ and centrifuged for 16 h at 29000 rpm at 20° C. in a TST 41 rotor (Kontron). At the end of the run most of the supernatant is removed and the tube is drained by quickly inverting. The glazy RNA pellet is dissolved in 0.4 ml of 10 mM Tris-HCl, pH 7.5 and 0.2% SDS by vortexing and occasional warming (2 min) at 37° C. The RNA is precipitated by addition of 1 ml of ethanol and centrifugation in an Eppendorf centrifuge for 5 min. The RNA (1.1 mg) is air dried and dissolved in 0.5 ml of elution buffer. After heating for 2 min at 68° C. and chilling on ice, 55 µl of 5 M NaCl are added and the solution is applied to a 2 ml column of oligo-dT cellulose (type 7, P-L Biochemicals) equilibrated in wash buffer. After three subsequent applications of the sample the column is washed with 15 ml of wash buffer, and the bound RNA eluted with 4 ml of elution buffer. The eluted material is heated for 2 min at 68° C., chilled and 0.44 ml of 5 M NaCl are added. The solution is applied to the re-equilibrated oligo-dT cellulose column (3×). After washing with 15 ml of wash buffer the bound RNA is eluted with 4 ml of elution buffer. The RNA is precipitated overnight at −20° C. by addition of 0.25 ml of 3 M NaOAc pH 5.5 and 10 ml of ethanol. The precipitate (76 µg) is collected by centrifugation (15 min at 16000 g), dissolved in 0.4 ml $H_2O$ and re-precipitated by addition of 25 µl of 3 M NaOAc and 1 ml of ethanol. After chilling in dry-ice for 10 min the RNA is collected by centrifugation for 5 min in an Eppendorf centrifuge. The pellet is air dried and dissolved in 75 µl of $H_2O$.

6.3. Preparation of cDNA: 10 µl (1 mg/ml) of the RNA solution is incubated in a solution containing 25 µl RVT buffer, 2.5 µl dNTP mix (20 mM of dATP, dCTP, dTTP and dGTP each), 5 µl of 1 mg/ml oligo-dT$_{12-18}$ (P-L Biochemicals), 1 µl $\alpha$-$^{32}P$-dCTP (10 µCi, 3000 Ci/mmol), 3 µl RNASIA™ (60 units, Biotec), 3 µl reverse transcriprase (66 units, Genofit), and 2 µl of $H_2O$. The mixture is incubated for 1.5 h at 42° C., then the reaction stopped by addition of 2 µl 0.5 M EDTA, pH 7.5. The RNA is degraded by addition of 25 µl 0.15 M NaOH and incubation at 65° C. for 1 h. The solution is neutralized by addition of 25 µl of 1 M Tris-HCl, pH 8.0 and 6 µl of 1 M HCl. 2 µl of 20% SDS are added and the solution is extracted with 0.15 ml phenol-chloroform mix (equal volumes of phenol and chloroform, 0.1% δ-hydroxyquinoline and equilibrated with 10 mM Tris-HCl, pH 8.0, 1 mM EDTA and 0.1 M NaCl). The aqueous phase is applied to a 2 ml EPHADEX® G-50 (medium) column in a Pasteur pipet equilibrated with TNE buffer. The breakthrough fraction (0.4 ml) containing 3 µg of cDNA is collected, and the cDNA precipitated by addition of 1 ml ethanol and chilling in dry-ice for 10 min. After centrifugation (5 min, Eppendorf centrifuge) the air-dried pellet is dissolved in 32 µl $H_2O$. The cDNA is extended with oligo-dC tails in a reaction mixture containing 32 µl cDNA (2.8 µg), 10 µl 1 M potassium cacodylate, pH 7.0, 5 µl 10 mM $CoCl_2$, 5 µl 1 mM DTT and 10 µCi of $^3H$-dCTP (20 Ci/mmol, 10 µl lyophylized). After preincubation for 5 min at 37° C. 3 µl of terminal deoxynucleotidyl transferase (81 units, P-L Biochemicals) are added and incubation is allowed to proceed for 10 min. 50 µl of TNE buffer are added and the solution is extracted with 0.1 ml phenol-chloroform mix. The cDNA is precipitated by addition of 0.1 ml ethanol and chilling in dry-ice. After centrifugation the pellet is washed with 70% ethanol, air-dried and dissolved in 13 µl of $H_2O$.

6.4. Preparation of ds cDNA: Above solution of cDNA in 13 µl $H_2O$, 25 µl RVT buffer, 2.5 µl dNTP mix (20 mM of dATP, dCTP, dTTP and dGTP each), 5 µl 0.2 mg/ml oligo-dG$_{12-18}$ (P-L Biochemicals), 3 µl $\alpha$-$^{32}P$-dCTP (10 mCi/ml, 3000 Ci/mmol) and 3 µl of reverse transcriprase (66 units, Genofit) are incubated at 42° C. for 1.5 h. The reaction is stopped by addition of 2 µl 0.5 M EDTA, pH 7.5 and 50 µl TNE buffer, and the mixture is extracted with 0.15 ml phenol-chloroform mix. The aqueous phase is applied onto a EPHADEX® G-50 column (2.5 ml in TNE buffer) and the breakthrough fraction (0.4 ml) containing 1.8 µg of ds cDNA is collected. The DNA is precipitated by addition of 1 ml ethanol and chilling in dry-ice. The resulting pellet is taken up in 32 µl $H_2O$ and the DNA extended with oligo-dC tails as described in Example 6.3 for single-stranded cDNA. The reaction is stopped by addition of 1 µl 0.5 M EDTA, pH 7.5, and the sample loaded onto a horizontal 1% agarose gel in TBE buffer using slots with a width of 0.5 cm. After electrophoresis for 1 h at 5 V/cm, the region containing cDNA with an approximate size between 1.5 and 2 kilobases is excised and placed in two micro-collodion bags (Sartorius) and presoaked in $H_2O$. 0.3 ml $H_2O$ are added and the bags are placed in an electrophoresis apparatus containing half-concentrated TBE buffer. The DNA is electroeluted at 5 V/cm electrode distance for 20 min and recovered from the bag by vigorous pipetting. After extraction with 0.6 ml phenol-chloroform mix, 40 µl of 3 M NaOAc pH 5.5 and 1.2 ml ethanol are added and the solution chilled in dry-ice for 10 min. After centrifugation (5 min, Eppendoff centrifuge) 90 ng of ds cDNA are recovered and dissolved in 20 µl of 10 mM Tris-HCl, pH 8.0 and 1 mM EDTA.

6.5. Annealing of cut pUC9 with poly(dG) tails to ds cDNA with poly(dC) tails and transformation of *E. coli* with the obtained plasmid: 20 µl cDNA (90 ng of size-fractionated material of Example 6.4) is mixed with 8 µl (100 ng) of oligo-$dG_{10-20}$ tailed pUC9 DNA (Pharmacia) and 172 µl TNE buffer and sequentially incubated at 65° C. for 10 min, at 46° C. for 1 h, at 37° C. for 1 h and at room temperature for 1 h. The annealed cDNA-plasmid DNA is used to transform competent *E. coli* HB 101 cells (strain LM 1035), which have been prepared for transformation as described in the Maniatis handbook. 1 µl of annealed DNA is added to 200 µl of competent cells and left on ice for 30 min. This procedure is performed 60 times. After a heat shock of 90 sec and chilling in ice for 2 min, 0.8 ml of SOC medium is added per tube which is then incubated for 60 min at 37° C. SOC medium contains 2% Bacto trypton, 0.5% yeast extract (both from Gibco), 10 mM NaCl, 2.5 mM KCl, 10 mM $MgCl_2$, 5 mM $MgSO_4$ and 20 mM glucose. After the incubation all tubes are combined and plated out on 3 McConkey agar plates 415 cm) containing 50 µg/ml of ampicillin. The plates are incubated overnight at 37° C. The resulting 2500 recombinants per plate are lifted onto nylon membranes (Pall-Biodyne) and two replicas made. The master filter is stored at 4° C. on an agar plate and the replicas are processed for colony hybridization as described in the Maniatis handbook.

EXAMPLE 7

Hybridization of human cDNA derived from glioma cell with cDNA coding for rat GdNPF The cDNA insert from 1 µg plasmid coding for rat GdNPF obtained from the positive clone of Example 5 is removed by digestion with PsI restriction endonuclease, agarose gel electrophoresis and gel elution. The pure cDNA insert (100 ng) is rendered radioactive using a nick translation kit from Amersham (N.5000) following the instructions given by the supplier. The radioactive cDNA probe has a specific activity of $5 \times 10^8$ dpm/µg.

Figure 1:
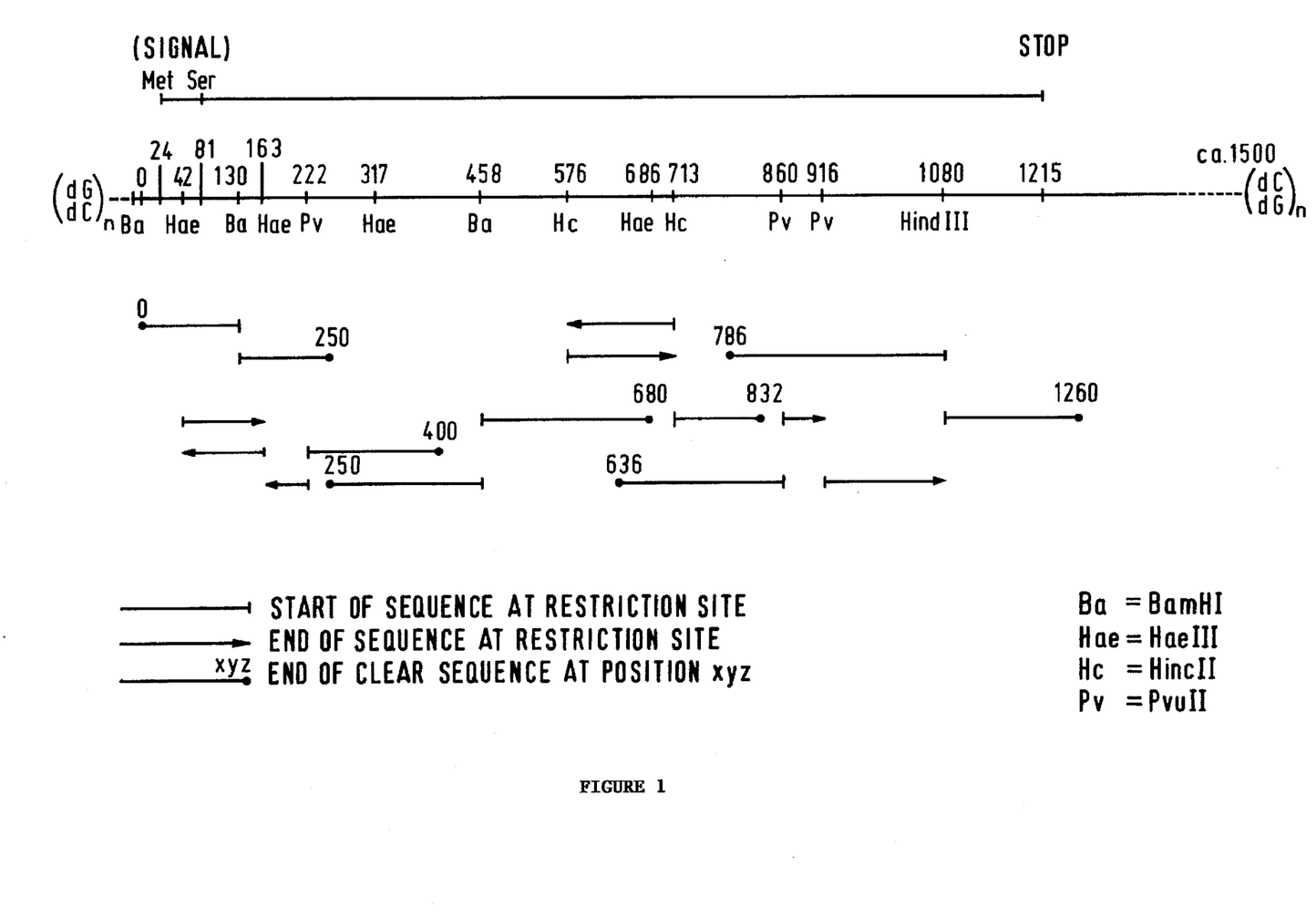
FIG. 1 is a summary of the restriction and sequence analysis of a double-stranded complementary DNA coding from human GdNPF.

The replica filters (Example 6.5) are prehybridized for 2 h in 100 ml of a solution containing 0.9 M NaCl, 0.18 M Tris-HCl, pH 8.0, 6 mM EDTA, 0.02% Ficoll 400, 0.02% polyvinylpyrrolidone, 0.02% BSA, 0.2% SDS and 50 µg/ml of denatured calf thymus DNA. Hybridization is performed overnight in 1 ml of the same solution containing the heat-denatured nick-translated cDNA probe ($60 \times 10^6$ dpm) in a sealed plastic bag. After hybridization the filters are washed in 200 ml of 0.9 M NaCl, 0.18 M Tris-HCl, pH 8.0, 6 mM EDTA and 0.2% SDS, twice at 65° C., followed by two washes at 65° C. with 200 ml of 0.45 M NaCl, 0.09 M Tris-HCl, pH 8.0, 3 mM EDTA and 0.2% SDS and two washes with 200 ml of 0.15 M NaCl, 0.03 M Tris-HCl, pH 8.0, 1 mM EDTA and 0.2% SDS. The filters are exposed on an X-ray film over night and positives appear on both replica filters. The eleven positive colonies are grown up and their plasmid DNAs are isolated for restriction analysis. Two recombinant plasmids containing inserts of approximately $1.5 \times 10^3$ nucleotides are chosen for restriction analysis as described in the Maniatis handbook and for determination of the full coding sequences using the method of Sanger (M13 cloning and sequencing handbook, Amersham). A summary of the restriction and sequence analysis is given in FIG. 1. The full sequence is depicted in formula IV. One clone gives a DNA of the formula IV, wherein W is A (hence $X_2$ is Arg), and the other clone gives a DNA sequence of the formula IV, wherein W is ACAG (hence $X_2$ is Thr—Gly).

EXAMPLE 8

Synthesis of human GdNPF by *E. coli* containing plasmids coding for human GdNPF One of the two clones of Example 7 shown to contain the DNA sequence of formula IV is grown in tryptone medium to an optical density ($OD_{650}$) of about 1. The cells are harvested and resuspended in 0.5 ml of an aqueous solution containing 30 mM NaCl and 50 mM Tris-HCl, pH 8.0. Lysozyme (Sigma) is added to 1 mg/ml. After 30 min. at 0° C., the suspensions are frozen in liquid nitrogen and thawed at 37° C. five times, then centrifuged for 20 min at 20 000 rpm in an SS 34 Sorvall rotor at 4° C. The supernatants are tested using the casein degradation assay of Example 2 and the neurite outgrowth assay of Example 9. The human GdNPF is purified by chromatography on heparin-Sepharose® CL-6B followed by chromatography on AFFI-GEL BLUE® (Cibacron Blue F3GA dye) as described for rat GdNPF by Guenther et al. [EMBO J. 4, 1963–1966 (1985)].

EXAMPLE 9

Neurite outgrowth assay

Culture dishes (35 mm) are inoculated with 40 000 EDTA-dislodged mouse neuroblastoma cells, clone $NB_2A$ (ATCC Cell Depository Number CCL 131), and incubated in DMEM containing 10% FCS at 37° C. in a humidified atmosphere containing 10% $CO_2$. After 16–18 h the medium is replaced by DMEM containing 0.5% FCS dialyzed exhaustively against 0.9% NaCl solution (but not heat inactivated), then filter-sterilized and frozen. After 22 h 100 µl of a cell supernatant of Example 8 in a final volume of 2.0 ml DMEM is added. The assay is terminated after 4 h by fixation of the cells with 2.5% glutaraldehyde in PBS. The extent of morphological differentiation is determined by phase contrast microscopy as described by D. Monard et al. [Proc. Nat. Acad. Sci. USA70, 1894–1897 (1973)].

EXAMPLE 10

Demonstration of relationship between novel human GdNPF and known rat GdNPF

About 250 µg of rat GdNPF [J. Guenther et al., EMBO J. 4, 1963–1966 (1985)] is reduced and carboxymethylated according to V. T. Ruegg et al. [Methods in Enzymology47, 111–116 (1977)]. The reaction mixture is dialyzed against 0.1% TFA, concentrated to 1 ml with a Savant Speed Vac concentrator and desalted by reversed phase high pressure liquid chromatography. The sample is injected on a wide-pore $C_8$-RP column 0.4×25 cm (Bakerbond™ RP 7105-0, J.

T. Baker) and processed with 0.1% TFA in a gradient of 40% to 50% aqueous acetonitrile in 30 min. The fraction containing the protein is freed from acetonitrile and concentrated to 0.5 ml (Savant Speed VAC concentrator). The resulting solution, 120 μl of 1 M NH$_4$HCO$_3$ and 2 μg trypsin (Worthington) in 10 μl 10$^{-3}$ M HCl are incubated for 24 h at 37° C. The reaction mixture is acidified to pH 2 with TFA and purified by high pressure liquid chromatography on the same column as above. The sample is processed with 0.1% aqueous TFA (5 min), then a gradient of 0.1% TFA in 0% to 50% aqueous acetonitrile in 90 min. Fractions containing five different polypeptides cleanly separated during the first half of the chromatography are collected and concentrated to 20 μl, then sequenced on a commercial gas-liquid phase sequencer (Applied Biosystems).

The following sequences are found:
1) Thr—Phe—Val—Ala—Gly—Asp—Gly—Lys, related to sequence 187 to 194 of human GdNPF, wherein Ala replaces $^5$Gly
2) Phe—Gln—Pro—Glu—Asn—Thr—Lys, identical with sequence 178 to 184 of human GdNPF,
3) Thr—Ile—Asn—Ser—Trp or Thr—Met—Asn—Thr—Met—Val—Pro—Lys, related to sequence 257 to 268 of human GdNPF,
4) Ala—Ile—Val—Ser—Lys, identical with sequence 79 to 83 of human GdNPF, and
5) Ala—Asn—Phe—Ala—Lys, identical with sequence 303 to 307 of human GdNPF.

These results indicate that the isolated human cDNA indeed corresponds to the coding sequence of GdNPF and does not represent an artifact.

EXAMPLE 11

Synthesis of GdNPF fragments

The peptides are synthesized using the solid-phase method developed by Merrifield [A. Marglin & R. B. Merrifield, Ann. Rev. Biochem. 39, 841–866 (1970)] with two minor modifications: The tert-butoxy-carbonyl-protected amino acids are activated for condensation by the addition of dicyclohexylcarbodiimide and 1-hydroxybenzotriazole [W. König & R. Geiger, Chem. Bet. 103, 788–798 (1979)], and the resin is washed alternatingly with solvents that favour swelling and extreme shrinking [L. Corley, D. M. Sachs & C. B Anfinsen, Biochem., Biophys. Res. Commun. 47, 1353–1359 (1972)].

11.1. Peptide synthesis protocol: The C-terminal amino acid is condensed with chloromethylated polystyrene resin (Merrifield polymer, FLUKA, Buchs, Switzerland) according to the procedure of B. F. Gisin [Helv. Chim. Acta 56, 1476–1482 (1973)]. The peptide synthesis is carried out manually in a reactor designed by M. A. Juillerat (Nestec SA, Switzerland). Mixing is achieved by flushing nitrogen through the reactor vessel.

A reaction cycle consists of:
(a) 50% TFA/CH$_2$Cl$_2$, 5 min
(b) 50% TFA/CH$_2$Cl$_2$, 25 min
(c) CH$_2$Cl$_2$, three times 2 min
(d) CHCl$_3$, three times 2 min
(e) triethylamine/CHCl$_3$ 1:9, twice 5 min
(f) CHCl$_3$, three times 2 min
(g) dimethylformamide (DMF), three times 2 min
(h) 4 equivalents tert-butoxycarbonyl-protected amino acid and 4 equivalents 1-hydroxybenzotriazole in DMF, followed after 1 min by 4 equivalents dicyclohexylcarbodiimide in CH$_2$Cl$_2$ 60 min
(i) DMF, twice 2 min
(j) CH$_2$Cl$_2$, twice 2 min
(k) CH$_3$OH, twice 5 min
(l) CH$_2$Cl$_2$, three times 2 min
(m) second coupling with 2.5 equivalents of the same protected amino acid, steps (d)–(l)
(n) 1% N-acetylimidazole and 10% acetic anhydride in CH$_2$Cl$_2$, 30 min.

The following N$^\alpha$-tert-butyloxycarbonyl(N-BOC)-L-amino acids (Bachem Fine Chemicals, Bubendorf, Switzerland) are used:

N-BOC-L-alanine
N -BOC-N-nitro-L-arganine
N-BOC-L-aspartic acid-β-cyclohexylester
N-BOC-L-glutamine
N-BOC-L-glutamic acid-γ-benzylester
N-BOC-L-glycine
N$^\alpha$-BOC-N$^{im}$-tosyl-L-histidine
N-BOC-L-isoleucine
N$^\alpha$-BOC-N$^\epsilon$-2-chlorobenzyloxycarbonyl-L-lysine
N-BOC-L-phenylalanine
N-BOC-L-proline
N-BOC-O-benzyl-L-serine
N-BOC-O-benzyl-L-threonine
N-BOC-L-tryptophane
N-BOC-L-valine A larger excess of 6 to 8 equivalents is used in the coupling of steps (h) and (m) with the tert-butoxycarbonyl-protected amino acids aparagine, glutamine, isoleucine, proline, and threonine. In the cycles following addition of a tryptophane residue, 2% 1,2-ethanedithiol (FLUKA) is added to the deprotection steps (a) and (b) in order to prevent the oxidation of the indole ring. Dehydration of the carboxamide function of glutamine is minimized by preforming the 1-hydroxybenzotriazole ester (0°, 15 min) before addition to the resin in step (h).

11.2. Gln—Lys—Ala—Lys—Ile—Glu—Val—Ser—Glu—Asp—Gly—Thr—Lys—Ala: The reactor vessel is charged with 3.55 g (1.92 mmol) of alanyl-substituted resin (0.54 mmol/g resin), and 13 cycles with the corresponding amino acids are run. The peptide synthesis is monitored by ninhydrin analysis of small aliquots. The final peptide-resin is treated with 35 ml of hydrogen fluoride/anisole (10:1, v/v) for 1 hour at 0° C. The hydrogen fluoride is removed at 0° C. under reduced pressure. The resin is washed three times with ethyl acetate, then extracted with three portions of 50 ml 50% acetic acid. The extracts are lyophilized, and the residue purified by high pressure liquid chromatography using a Whatman preparative column PARTISIL™ 10 ODS-3, 25 cm, using 0.1% TFA (10 min), then 0.1% TFA in a gradient of 0 to 50% acetonitrile (60 min). The pure product is characterized by amino acid sequencing on a commercial gas-liquid phase sequences (Applied Biosystems).

11.3. His—Lys—Ala—Lys—Ile—Glu—Val—Ser—Glu—Asp—Gly—Thr—Lys—Ala: This protein is prepared in a manner completely analogous to Example 11.2 except for substituting histidine for glutamine in the last cycle.

11.4. Arg—Ser—Ser—Pro—Pro—Trp—Phe—Ile—Val—Asp—Ser—Phe: The reactor vessel is charged with 3.0 g (1.29 mmol) of phenylalanyl-substituted resin (0.43 mmol/g resin), and 11 cycles with the corresponding amino acids are run. Cleavage, deprotection and purification of the product is performed as described in Example 11.2 except that the hydrogen fluoride/anisol mixture additionally contains 2% 1,2-ethanedithiol.

11.5. Lys—Ser—Arg—Phe—Gln—Pro—Glu—Asn—Thr—Lys—Lys—Arg—Thr—Phe: This protein is prepared in a manner analogous to Example 11.4 in 13 cycles with the corresponding amino acids.

EXAMPLE 12

Pharmaceutical preparation for parenteral application

200 μg of human GdNPF are dissolved in 3 ml of 5N human serum albumin. The resulting solution is passed through a bacteriological filter and the filtered solution subdivided under aseptic conditions into 10 vials. The vials are preferably stored in the cold, for example at −20° C.

We claim:

1. A method of inducing neurite extension in a cultured neuronal cell comprising:

contacting a cultured neuronal cell with an effective amount of a protein, wherein the protein has an amino acid sequence:

| | |
|---|---:|
| Ser—His—Phe—Asn—Pro—Leu—Ser—Leu—Glu—Glu—Leu—Gly—Ser—Asn—Thr—Gly— | 16 |
| Ile—Gln—Val—Phe—Asn—Gln—Ile—Val—Lys—Ser—Arg—Pro—His—Asp—Asn—Ile | 32 |
| Val—Ile—Ser—Pro—His—Gly—Ile—Ala—Ser—Val—Leu—Gly—Met—Leu—Gln—Leu— | 48 |
| Gly—Ala—Asp—Gly—Arg—Thr—Lys—Lys—Gln—Leu—Ala—Met—Val—Met—Arg—Tyr— | 64 |
| Gly—Val—Asn—Gly—Val—Gly—Lys—Ile—Leu—Lys—Lys—Ile—Asn—Lys—Ala—Ile— | 80 |
| Val—Ser—Lys—Lys—Asn—Lys—Asp—Ile—Val—Thr—Val—Ala—Asn—Ala—Val—Phe | 96 |
| Val—Lys—Asn—Ala—Ser—Glu—Ile—Glu—Val—Pro—Phe—Val—Thr—Arg—Asn—Lys | 112 |
| Asp—Val—Phe—Gln—Cys—Glu—Val—Arg—Asn—Val—Asn—Phe—Glu—Asp—Pro—Ala— | 128 |
| Ser—Ala—Cys—Asp—Ser—Ile—Asn—Ala—Trp—Val—Lys—Asn—Glu—Thr—Arg—Asp— | 144 |
| Met—Ile—Asp—Asn—Leu—Leu—Ser—Pro—Asp—Leu—Ile—Asp—Gly—Val—Leu—Thr— | 160 |
| Arg—Leu—Val—Leu—Val—Asn—Ala—Val—Tyr—Phe—Lys—Gly—Leu—Trp—Lys—Ser— | 176 |
| Arg—Phe—Gln—Pro—Glu—Asn—Thr—Lys—Lys—Arg—Thr—Phe—Val—Ala—Ala—Asp— | 192 |
| Gly—Lys—Ser—Tyr—Gln—Val—Pro—Met—Leu—Ala—Gln—Leu—Ser—Val—Phe—Arg— | 208 |
| Cys—Gly—Ser—Thr—Ser—Ala—Pro—Asn—Asp—Leu—Trp—Tyr—Asn—Phe—Ile—Glu— | 224 |
| Leu—Pro—Tyr—His—Gly—Glu—Ser—Ile—Ser—Met—Leu—Ile—Ala—Leu—Pro—Thr— | 240 |
| Glu—Ser—Ser—Thr—Pro—Leu—Ser—Ala—Ile—Ile—Pro—His—Ile—Ser—Thr—Lys— | 256 |
| Thr—Ile—Asp—Ser—Trp—Met—Ser—Ile—Met—Val—Pro—Lys—Arg—Val—Gln—Val— | 272 |
| Ile—Leu—Pro—Lys—Phe—Thr—Ala—Val—Ala—Gln—Thr—Asp—Leu—Lys—Glu—Pro | 288 |
| Leu—Lys—Val—Leu—Gly—Ile—Thr—Asp—Met—Phe—Asp—Ser—Ser—Lys—Ala—Asn— | 304 |
| Phe—Ala—Lys—Ile—Thr—$X_1$—Ser—Glu—Asn—Leu—His—Val—Ser—His—Ile—Leu— | 320 |
| Gln—Lys—Ala—Lys—Ile—Glu—Val—Ser—Glu—Asp—Gly—Thr—Lys—Ala—Ser—Ala— | 336 |
| Ala—Thr—Thr—Ala—Ile—Leu—Ile—Ala—Arg—Ser—Ser—Pro—Pro—Trp—Phe—Ile— | 352 |
| Val—Asp—Arg—Pro—Phe—Leu—Phe—Phe—Ile—Arg—His—Asn—Pro—Thr—Gly—Ala— | 368 |
| Val—Leu—Phe—Met—Gly—Gln—Ile—Asn—Lys—Pro | 378 | wherein $X_1$ is Arg or Thr—Gly, wherein the protein is maintained in contact with the neuronal cell for a time sufficient to effect neurite extension in the neuronal cell.

2. The method of claim 1, wherein the protein is glycosylated.

3. The method of claim 1, wherein the protein contains an intramolecular disulfide bond between any two Cys residues.

4. The method of claim 1, wherein the nitrogen of the N-terminal Ser residue of the protein is covalently bound to a chemical moiety, wherein the chemical moiety is selected from the group consisting of an acyl group, an L-amino acid, and a peptide.

5. The method of claim 14 wherein the acyl group is formyl or alkanoyl.

6. The method of claim 5, wherein the alkanoyl is palmitoyl or myristoyl.

7. The method of claim 5, wherein the alkanoyl is a lower alkanoyl.

8. The method of claim 7, wherein the lower alkanoyl is acetyl or propionyl.

9. The method of claim 4, wherein the peptide is Met-Asn—Trp—His—Leu—Pro—Leu—Phe—Leu—Leu—Ala—Ser—Val—Thr—Leu—Pro—Ser—Ile—Cys, where the Cys residue of the peptide is covalently bound to the nitrogen of the N-terminal Ser residue of the protein.

10. The method of claim 9, wherein the peptide is acylated.

11. The method of claim 1, wherein the protein is combined with a pharmaceutically acceptable carrier.

\* \* \* \* \*

UNITED STATES PATENT AND TRADEMARK OFFICE
CERTIFICATE OF CORRECTION

PATENT NO. : 5,656,596
DATED : August 12, 1997
INVENTOR(S) : Monard et al.

It is certified that error appears in the above-identified patent and that said Letters Patent is hereby corrected as shown below:

<u>Column 30,</u>
Line 39, please delete "claim 14" and replace with -- claim 4 --.

Signed and Sealed this

Fifteenth Day of October, 2002

*Attest:*

*Attesting Officer*

JAMES E. ROGAN
*Director of the United States Patent and Trademark Office*